US008350118B2

(12) United States Patent
Amagai et al.

(10) Patent No.: US 8,350,118 B2
(45) Date of Patent: Jan. 8, 2013

(54) ALLERGIC DISEASE MODEL ANIMALS

(75) Inventors: Masayuki Amagai, Tokyo (JP); Akiharu Kubo, Tokyo (JP); Keisuke Nagao, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 12/736,800

(22) PCT Filed: May 15, 2009

(86) PCT No.: PCT/JP2009/002161
§ 371 (c)(1),
(2), (4) Date: Nov. 10, 2010

(87) PCT Pub. No.: WO2009/139191
PCT Pub. Date: Nov. 19, 2009

(65) Prior Publication Data
US 2011/0088103 A1    Apr. 14, 2011

(30) Foreign Application Priority Data

May 16, 2008  (JP) ................................ 2008-129597
Nov. 28, 2008  (JP) ................................ 2008-303926

(51) Int. Cl.
*A01K 67/027* (2006.01)
*C12N 5/00* (2006.01)
(52) U.S. Cl. ......................................... 800/18; 435/325
(58) Field of Classification Search .................... 800/18; 435/325
See application file for complete search history.

(56) References Cited

FOREIGN PATENT DOCUMENTS
JP    2001-321016 A    11/2001
JP    2004-166696 A    6/2004

OTHER PUBLICATIONS

Ryding et al, (J Endocrinol, 171: 1-14, 2001).*
Novak et al, (Journal of Invnestigative Dermatology, 128: 1430-1435, 2008).*
Pearson (Nature, 415:8-9 (Jan. 3, 2002).*
Lerbaek et al (British Journal of Dermatology, 157: 1199-1204, 2007).*
International Search Report mailed Jun. 16, 2009, in PCT/JP2009/002161, 2 pages.
Amagai, Masayuki, "Analysis on pathogenesis of atopic disease due to impaired barrier function," Kosei Rodo Kagaku Kenkyu Seika Database [online], Apr. 8, 2008, retrieved on Jun. 3, 2009 from the internet: Bunken Bango 200729027A, 2 pages, with English translation, 2 pages.
Amagai, Masayuki, "Barrier Kino Shogai ni yoru Atopic Shikkan Byotai Kaimei ni Kansuru Kenkyu Heisei 19 Nendo Sokatsu Kenkyu Hokoku," Kosei Rodo Kagaku Kenkyuhi Hojokin Men'eki Arrergy Shikkan Yobo-Cyiryo Kenkyu Jigyo, Mar. 2008, 1-61.
Palmer et al,. "Common loss-of-function variants of the epidermal barrier protein filaggrin are a major predisposing factor for atopic dermatitis," Nature Genetics, Apr. 2006, 38(4):441-446.
R.W. Old, translated by Mitsui Sekiguchi, Idenshi Sosa no Genri, Bairukan Co., Ltd., 2000, 5$^{th}$ Ed., p. 341.
Muramatsu et al., Ed., Jikken Igaku Bessatsu Shintei Idenshi Kogaku Handbook, Yodosha Co., Ltd., 1999, Revised 3$^{rd}$ Ed., 234-256.
Denecker et al., "Caspase-14 reveals its secrets," J. Cell Biol., Feb. 11, 2008, 180(3):451-458.
Denecker et al., "Caspase-14 protects against epidermal UVB photodamage and water loss," Nature Cell Biology, Jun. 2007, 9(6):666-674, and 5 pages Supplemental Information.
Hara-Chikuma et al., "Epidermal-Specific Defect of GPI Anchor in *Pig-a* Null Mice Results in Harlequin Ichthyosis-Like Features," J. Invest. Dermatol., 2004, 123(3):464-469.
Carninci et al., "Genome-wide analysis of mammalian promoter architecture and evolution," Nature Genetics, Jun. 2006, 38(6):626-635, and two pages Corrigenda.
Hayashizaki et al., "Discovery of novel mechanisms to control gene expression (Structure of promoters implicate function)," Press Release—The Genome Network and FANTOM Consortium Genomic Sciences Center, 2006, retrieved Jun. 4, 2009, 6 pages, with English translation, 4 pages.
Matsuoka et al., "Establishment of antigen-specific IgE transgenic mice to study pathological and immunobiological roles of IgE in vivo," International Immunology, 1999, 11(6):987-994.
Yoshimoto et al., "IL-18 induction of IgE: dependence on CD4$^+$ T cells, IL-4 and STAT6," Nature Immunology, Aug. 2000, 1(2):132-137.
Yamanaka et al., "Skin-Specific Caspase-1-Transgenic Mice Show Cutaneous Apoptosis and Pre-Endotoxin Shock Condition with a High Serum Level of IL-18," J. Immunol., 2000, 165:997-1003.
Tsukuba et al., "Association of Cathepsin E Deficiency with Development of Atopic Dermatitis," J. Biochem., 2003, 134:893-902.
Smith et al., "Loss-of-function mutations in the gene encoding filaggrin cause ichthyosis vulgaris," Nature Genetics, Mar. 2006, 38(3):337-342.
Nomura et al., "Unique mutations in the filaggrin gene in Japanese patients with ichthyosis vulgaris and atopic dermatitis," J. Allergy Clin. Immunol., Feb. 2007, 119(2):434-440.
Rothnagel et al,. "Characterization of the Mouse Loricrin Gene: Linkage with Profilaggrin and the Flaky Tail and Soft Coat Mutant Loci on Chromosome 3," Genomics, 1994, 23:450-456.
Presland et al., "Loss of Normal Profilaggrin and Filaggrin in Flaky Tail (ft/ft) Mice: an Animal Model for the Filaggrin-Deficient Skin Disease Ichthyosis Vulgaris," J. Invest. Dermatol., Dec. 2000, 115(6):1072-1081.

(Continued)

*Primary Examiner* — Gerald Leffers, Jr.
*Assistant Examiner* — Magdalene Sgagias
(74) *Attorney, Agent, or Firm* — Foley & Lardner LLP

(57) ABSTRACT

The object of the present invention is to provide a mouse model for allergic diseases such as atopic dermatitis, and a dermatitis mouse model with impaired skin-barrier function. The present inventors found out that a mouse that has been caused to completely lose the function of expressing profilaggrin protein and filaggrin protein by entirely or partially disrupting the endogenous gene encoding filaggrin by a genetic mutation such as deletion or replacement, can be used as a mouse model for allergic diseases or atopic dermatitis wherein the skin-barrier function has been impaired.

1 Claim, 13 Drawing Sheets

OTHER PUBLICATIONS

Kitagaki et al., "Immediate-Type Hypersensitivity Response Followed by a Late Reaction Is Induced by Repeated Epicutaneous Application of Contact Sensitizing Agents in Mice," J. Invest. Dermatol., Dec. 1995, 105(6):749-755.

Spergel et al.,, "Epicutaneous Sensitization with Protein Antigen Induces Localized Allergic Dermatitis and Hyperresponsiveness to Methacholine after Single Exposure to Aerosolized Antigen in Mice," J. Clin. Invest., Apr. 1998, 101(8):1614-1622.

Fallon et al., "A homozygous frameshift mutation in the mouse *Flg* gene facilitates enhanced percutaneous allergen priming," Nature Genetics, May 2009, 41(5):602-608.

* cited by examiner

[Fig. 1]
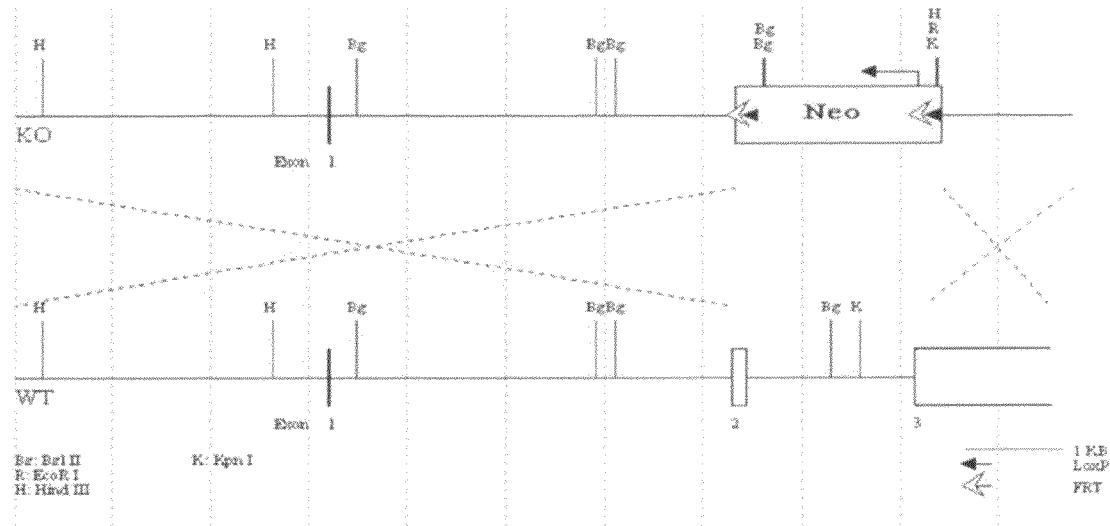
[Fig. 2]
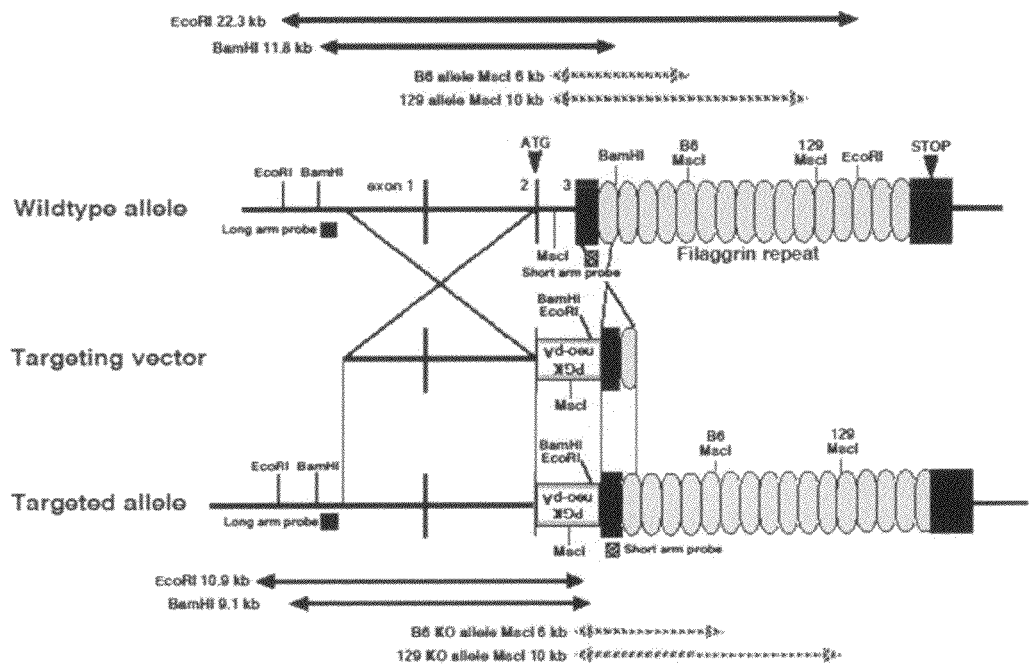

[Fig. 3]
ES clone 824: EcoRI digestion
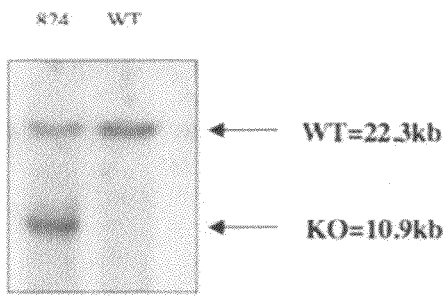
Southern blotting
EcoRI digestion
WT allele: 22.3K
KO allele: 10.9K
BamHI digestion
WT allele: 11.8K
KO allele: 9.1K
[Fig. 4-a]
F1 hetero mouse: BamHI digestion
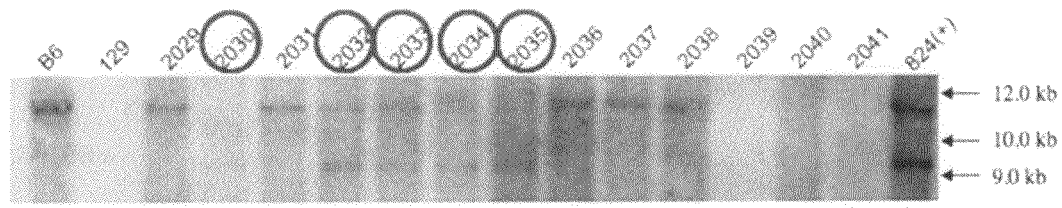

[Fig. 4-b]
Mscl digestion: Southern blotting with short arm probe
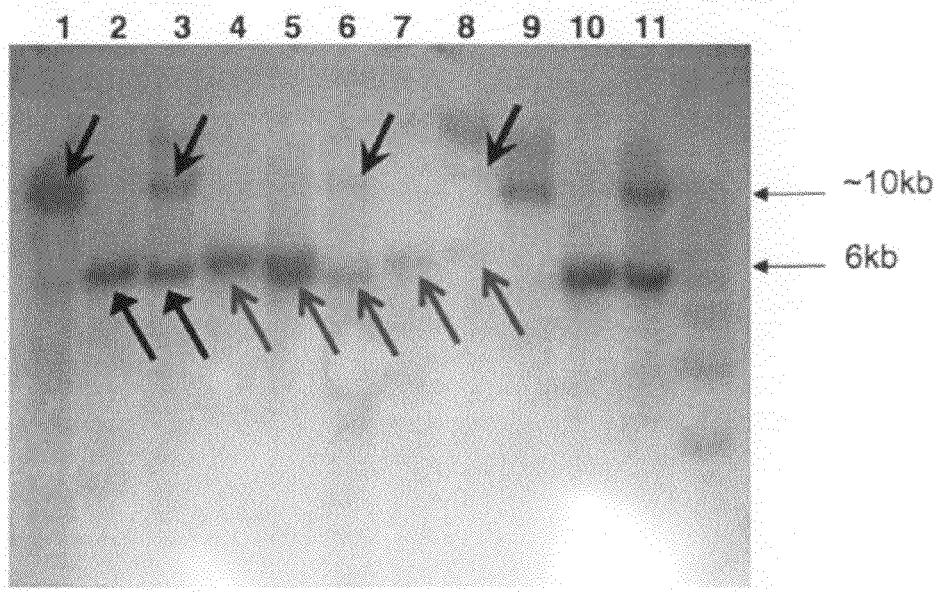
Lanes 1 and 9: 129 WT DNA
Lanes 2 and 10: B6 WT DNA
Lanes 3 and 11: Hybrid WT DNA
Lane 4: Mouse #2030 (female; has KO band hybridized with LA probe)
Lane 5: Mouse #2033 (female; has KO band hybridized with LA probe)
Lane 6: Mouse #2040 (WT littermate)
Lane 7: Mouse #2041 (male; has KO band hybridized with LA probe)
Lane 8: Clone #824
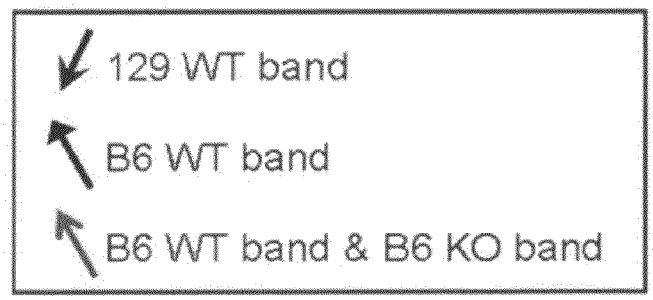

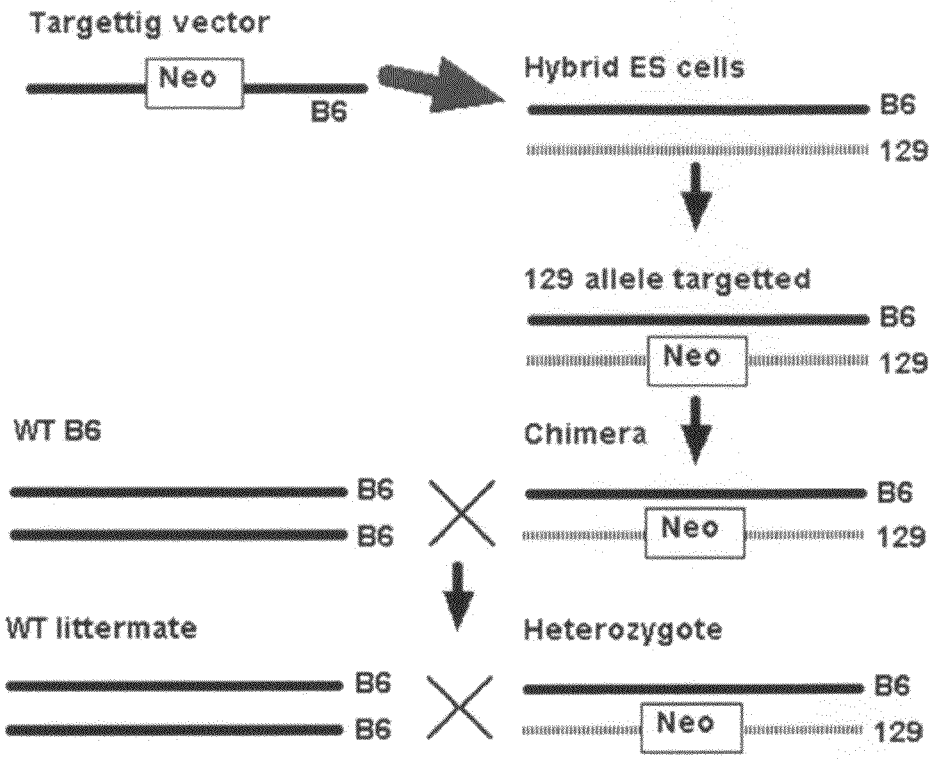
[Fig. 4-c]
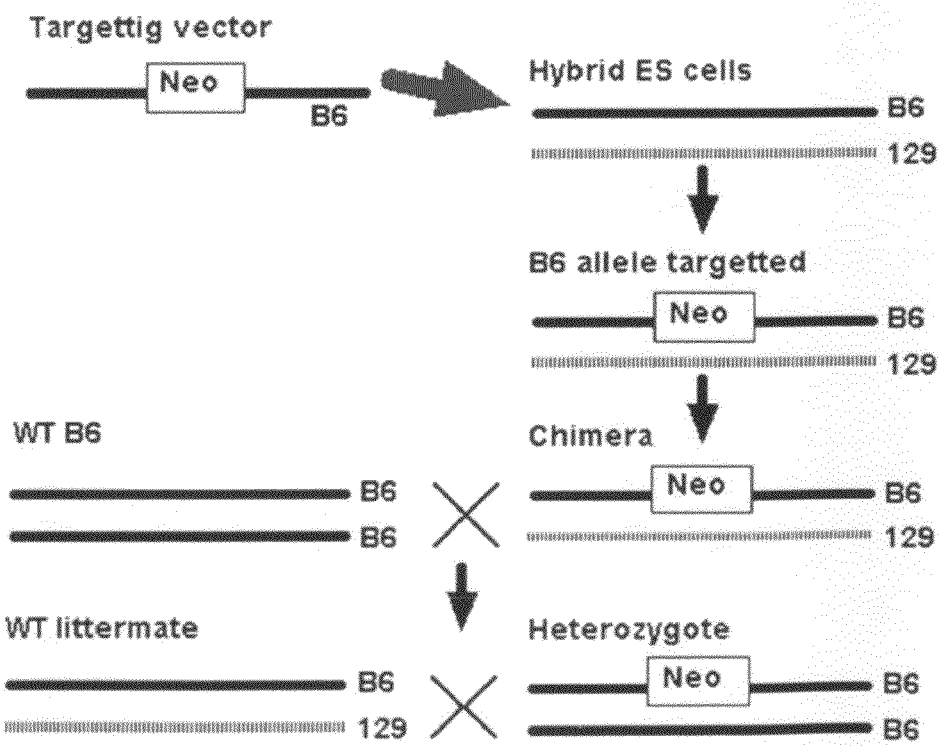
[Fig. 4-d]

[Fig. 5-a]
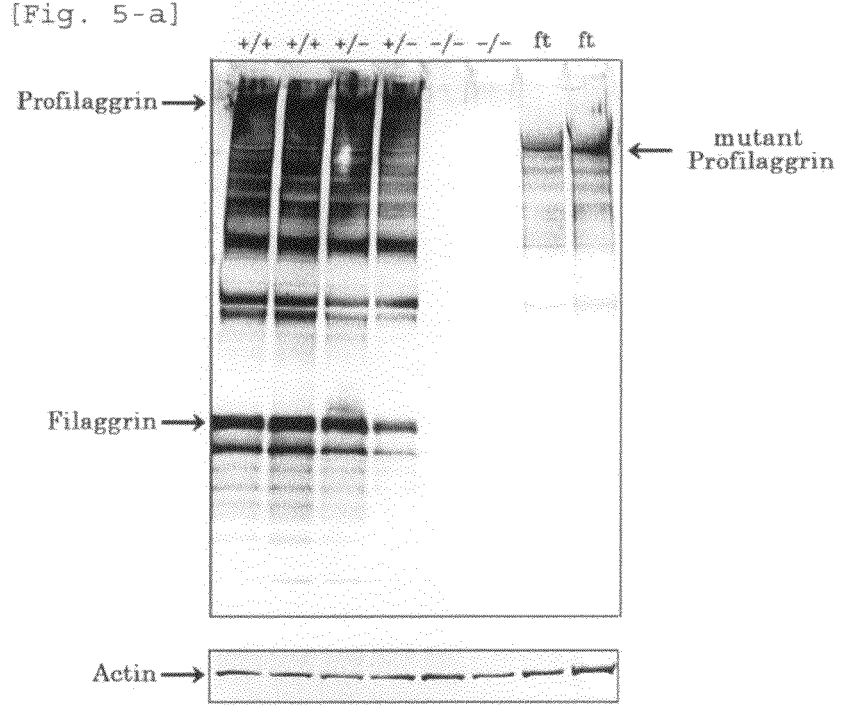
[Fig. 5-b]
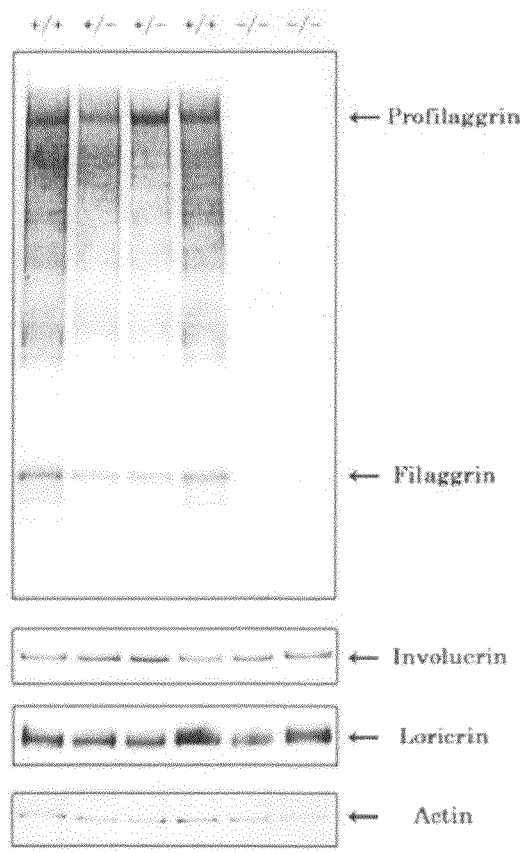

[Fig. 6]
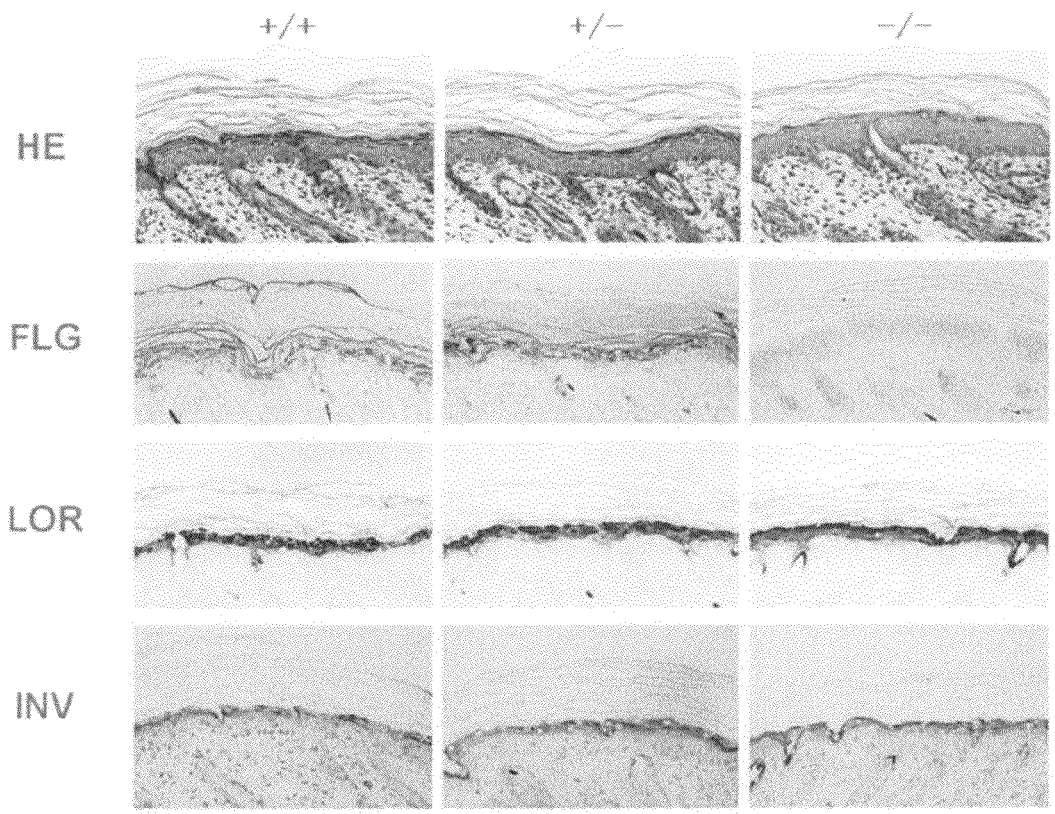
[Fig. 7]
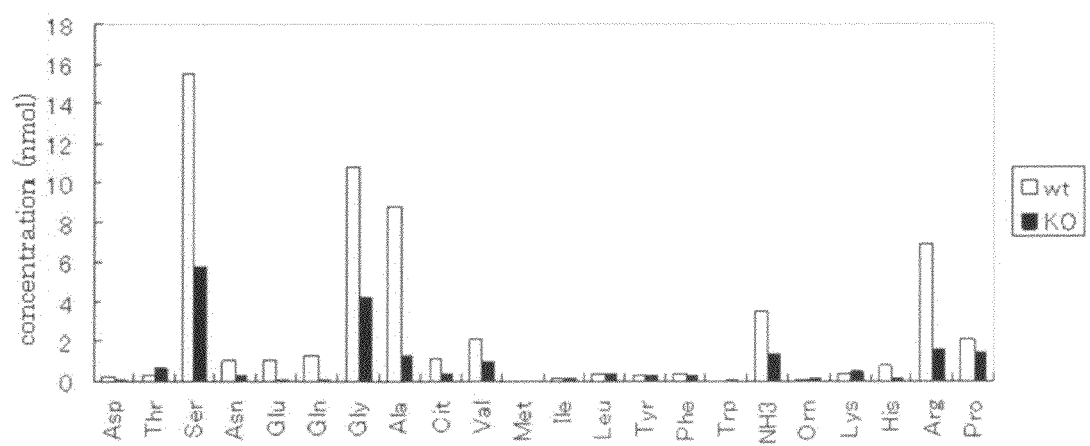

[Fig. 8]
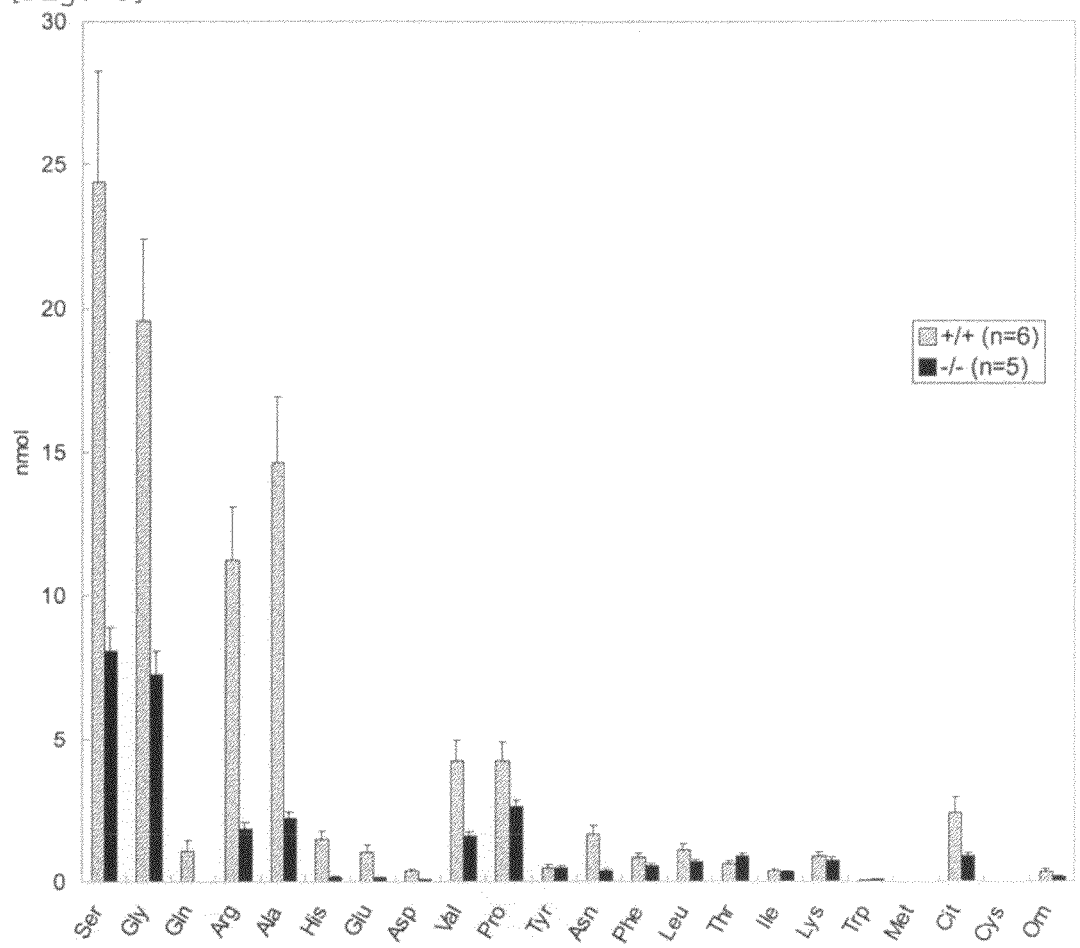
[Fig. 9]
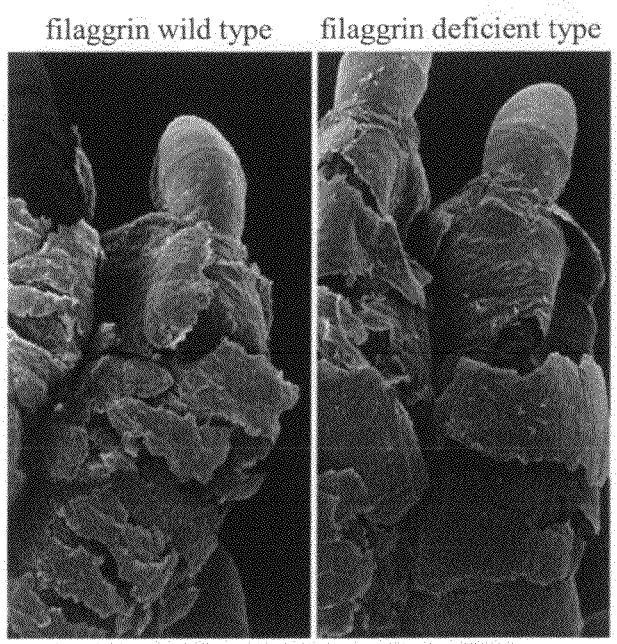
filaggrin wild type     filaggrin deficient type

[Fig. 10-a]
filaggrin wild type
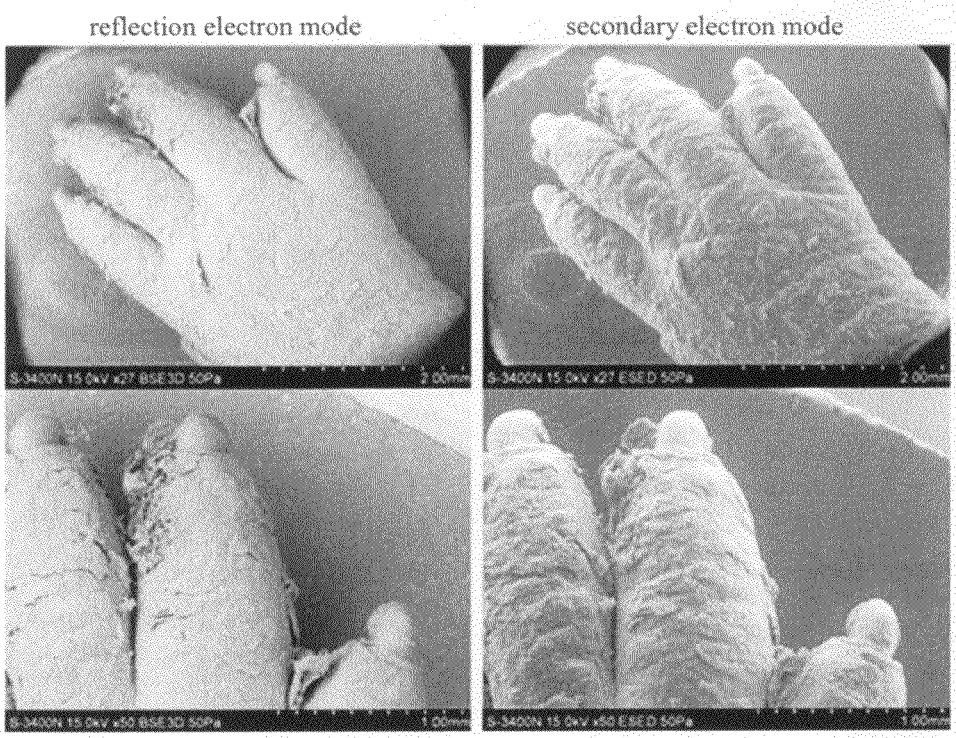
[Fig. 10-b]
filaggrin deficient type
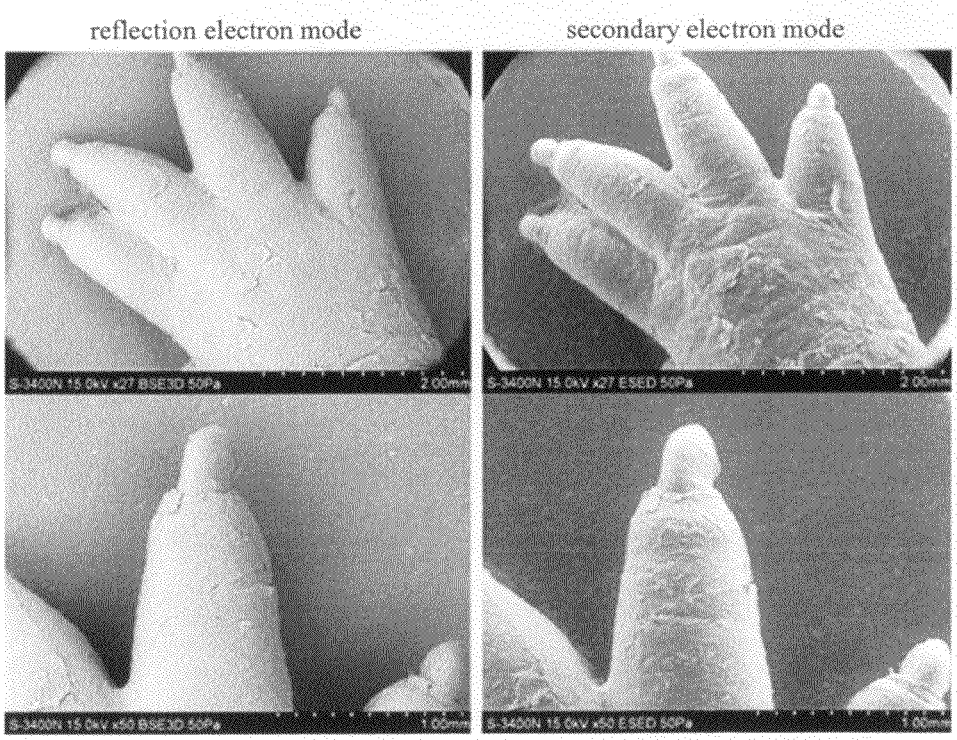

[Fig. 10-c]
filaggrin wild type
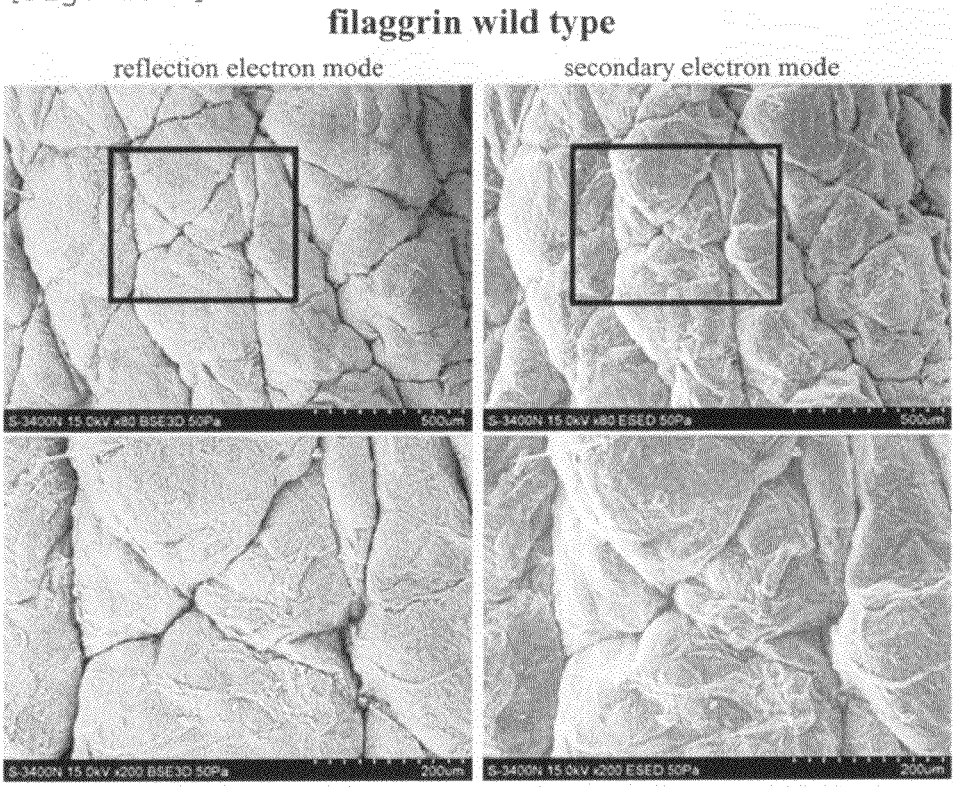
[Fig. 10-d]
filaggrin deficient type
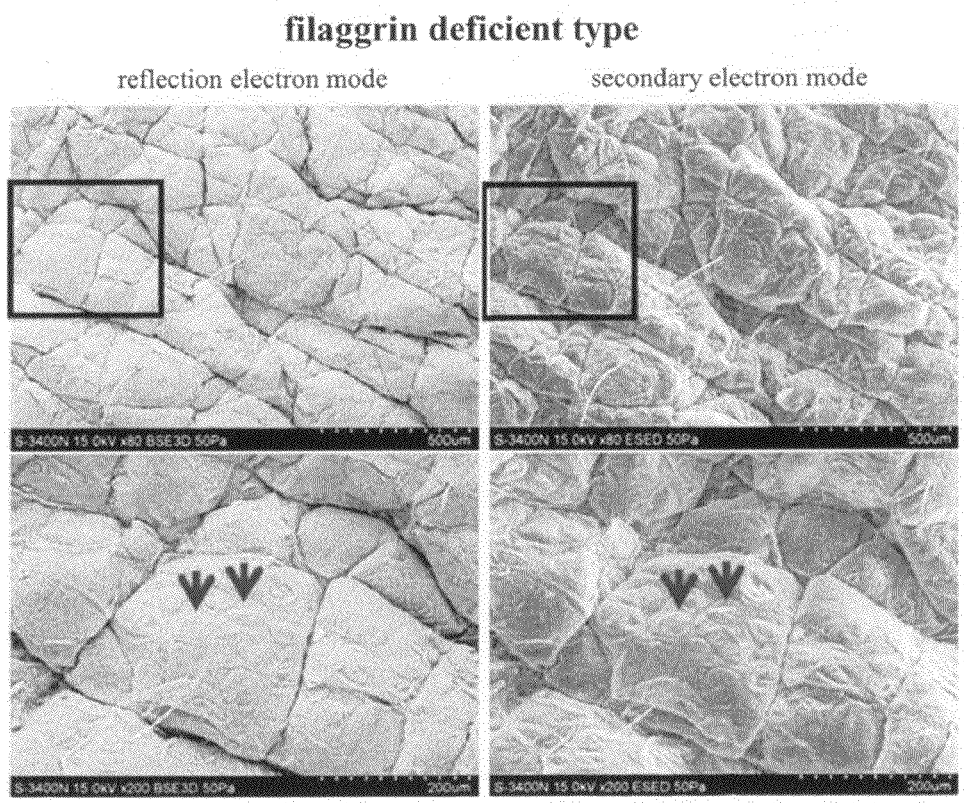

[Fig. 11-a]
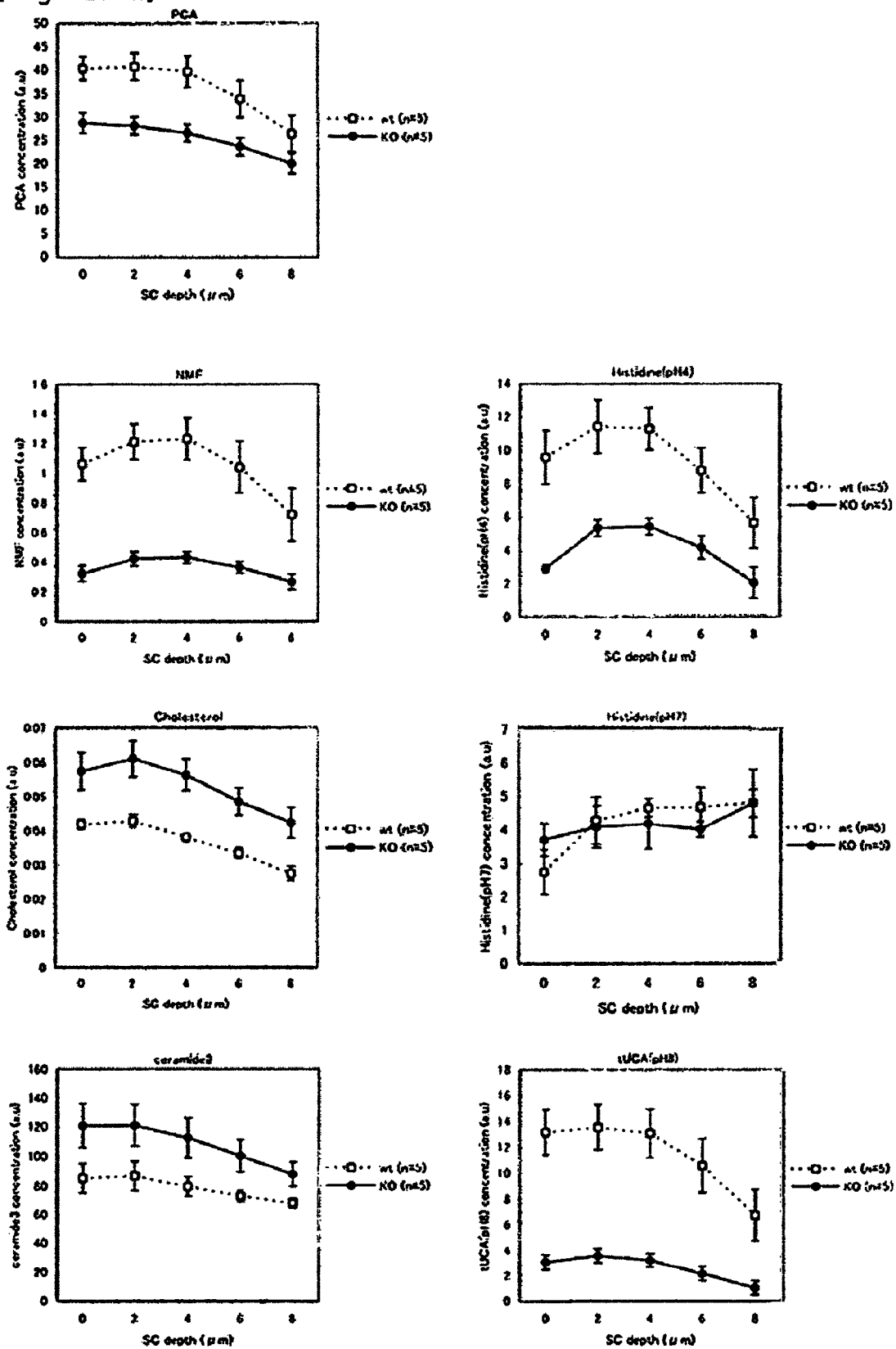

[Fig. 11-b]
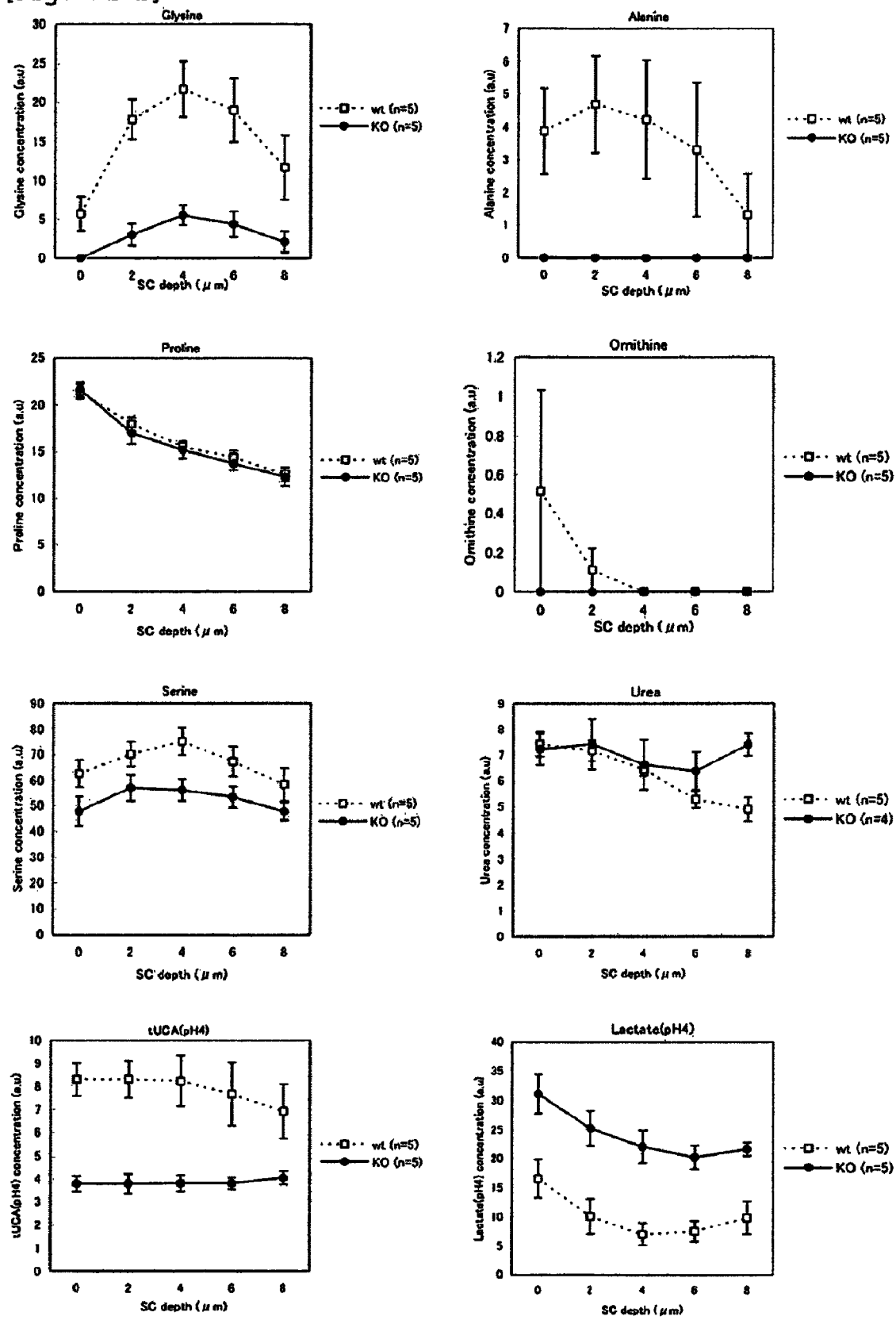

[Fig. 12]
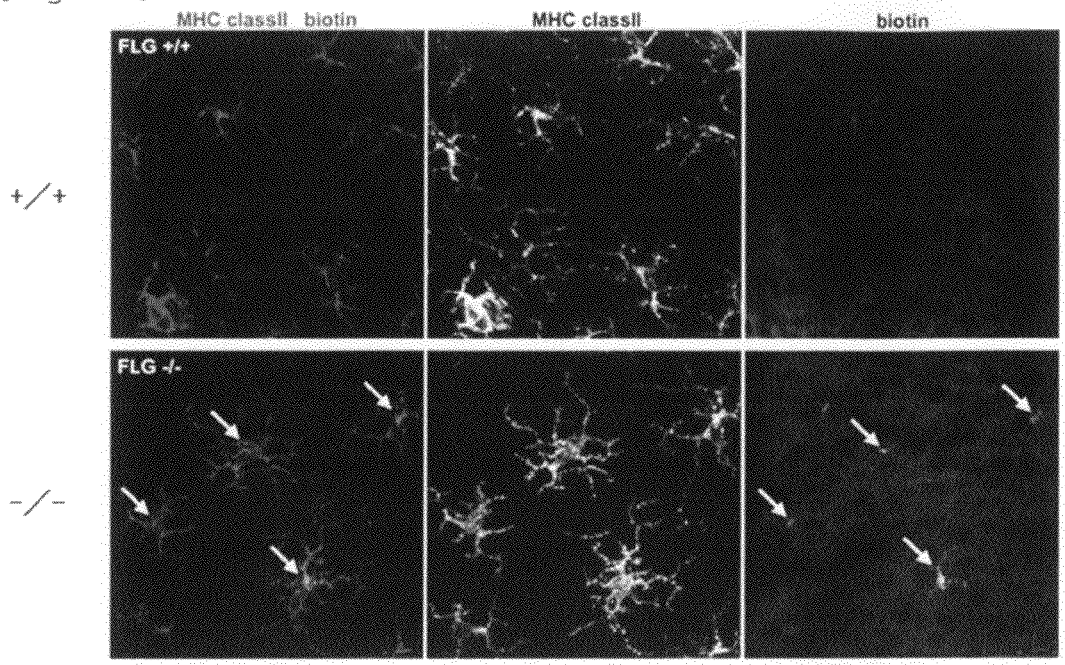
[Fig. 13]
wild type
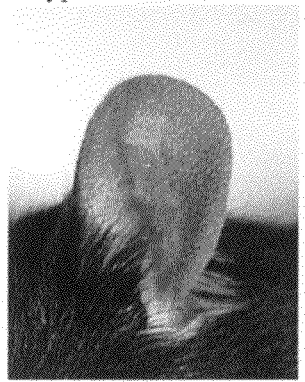 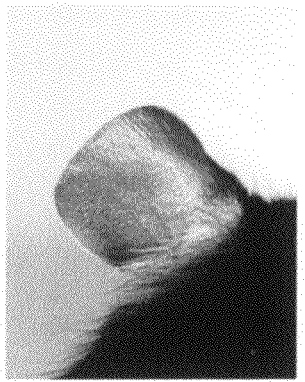
filaggrin deficient type
  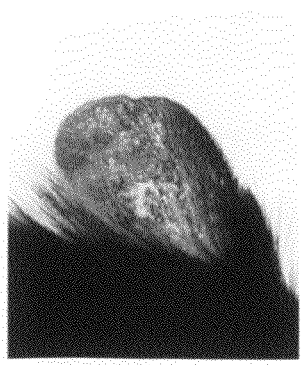

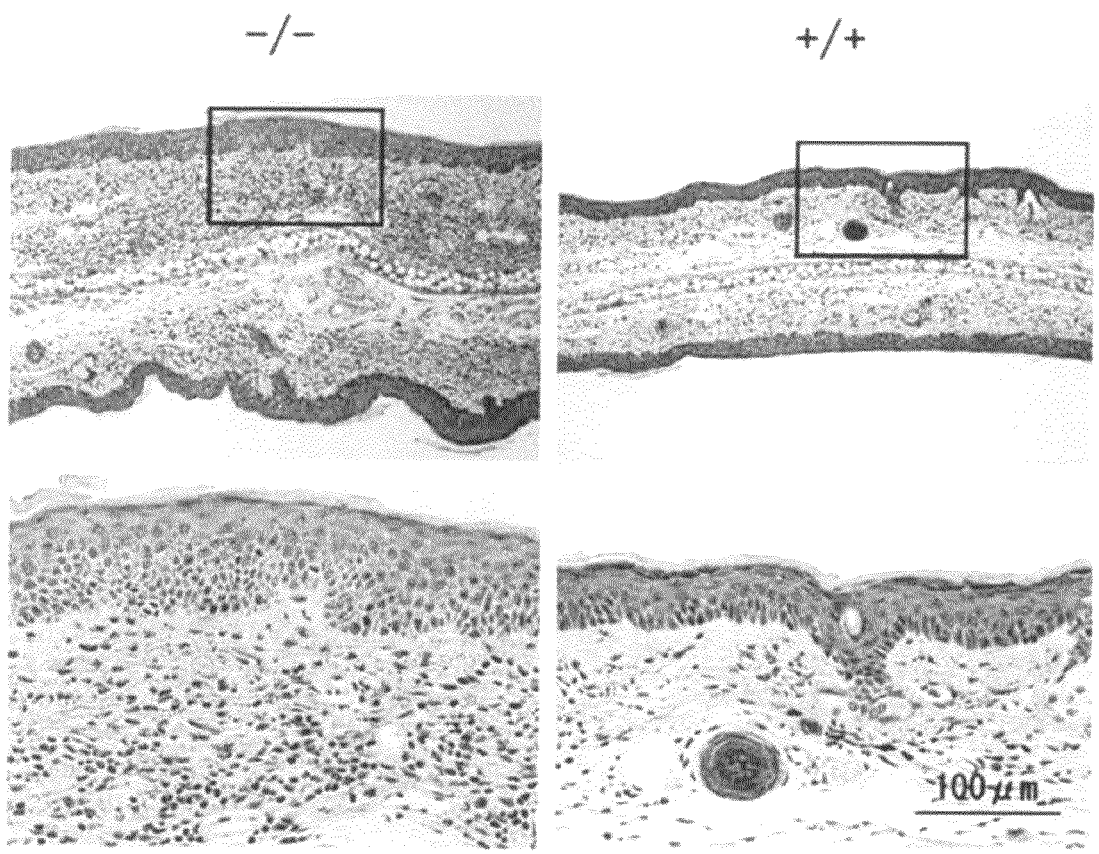
[Fig. 14]

ALLERGIC DISEASE MODEL ANIMALS

The instant application contains a Sequence Listing which has been submitted in ANSI format via EFS-WEB and is hereby incorporated by reference in its entirety. Said ANSI copy, created on Jan. 23, 2012, is named sequence.txt and is 5 KB.

TECHNICAL FIELD

The present invention relates to a method for using a mouse that has lost the function of expressing profilaggrin and filaggrin as an animal model for allergic diseases such as atopic dermatitis or as a dermatitis animal model with impaired skin-barrier function; and to an allergic disease mouse model or a dermatitis mouse model which has lost the function of expressing profilaggrin and filaggrin.

BACKGROUND ART

Atopic dermatitis is an inflammatory skin disease responsive mainly to external stimuli, which is an "environmental-genetic" disorder where the reaction to an environmental stimulation is influenced by a genetic background. Further, it has been known that in many cases atopic dermatitis patients also develop other allergic diseases such as bronchial asthma.

Heretofore, it has commonly been considered that atopic dermatitis is caused by some kind of immune abnormality, and a plurality of immune-related genes have been reported as genes responsible for atopic dermatitis. Thus, all atopic dermatitis model animals reported so far have been induced to develop a similar symptom to atopic dermatitis by introducing or knocking-out a gene associated with the regulation of an immune function. Examples of such atopic dermatitis animal model include GATA-3 transgenic mouse (Patent Document 1), TNP-IgE transgenic mouse (Non-patent Document 1), IL-18 transgenic mouse (Non-patent Document 2), Caspase-1 transgenic mouse (Non-patent Document 3), Cathepsin E-knockout mouse (Non-patent Document 4), etc.

More recently, however, it has been suggested that skin-barrier functional disorder may be associated with the pathogenesis of atopic dermatitis. The skin-barrier function is to retain water in the body or to protect against a substance entering from outside, ultraviolet rays, etc. and the stratum corneum that is the outermost layer of the epidermis fulfils a particularly important function. The stratum corneum is constituted by cornified keratinocytes and consists of a keratin-filament skeletal construct surrounded by a special coat which is not found in other cells in the body. For the construction of this keratin-filament skeleton, filaggrin derived from epidermal keratinocytes is indispensable. Filaggrin is a protein produced specifically in epidermal keratinocytes, and immediately after the precursor, profilaggrin protein, is expressed, it is phosphorylated and accumulated in keratohyaline granules and then processed into filaggrin through a dephosphorylation and hydrolysis. Filaggrin acts to aggregate keratin-filaments, and in addition, is degraded further into low-molecular peptides that function as a moisturizing factor or ultraviolet absorption factor.

As a result of a number of studies on atopic dermatitis patients in Europe and the United States, a genetic mutation that could trigger atopic dermatitis was discovered on the gene encoding filaggrin protein (FLG gene). It has been revealed that this genetic mutation causes a complete loss of profilaggrin protein and filaggrin protein (Non-patent Document 5), and that this mutation is frequently found in atopic dermatitis patients, and more frequently in atopic dermatitis patients also having asthma (Non-patent Document 6). Further, it has been demonstrated also in Japan that a similar genetic mutation to FLG is frequently found in atopic dermatitis patients (Non-patent Document 7). These results imply that impaired skin-barrier function due to filaggrin protein deficiency is associated with the pathologies of atopic dermatitis and asthma. The present situation is, however, that the relation between such skin-barrier functional disorder and allergic diseases such as atopic dermatitis has attracted little attention heretofore, which has prevented the promotion of further study. It is believed that for the future establishment of a method for preventing and treating atopic dermatitis and/or asthma, an animal model in which skin-barrier function has been impaired due to profilaggrin and filaggrin deficiency is very useful.

As a method for producing a skin-disease animal model characterized by impaired skin-barrier function, a method of physically separating the stratum corneum by tape-stripping and a method of removing a lipid component constituting the skin-barrier function by an organic solvent such as acetone or by a surfactant are known (for example, Patent Document 2, Non-patent Document 10, and Non-patent Document 11). These animal models, however, do not reflect the skin-barrier functional disorder due to filaggrin deficiency, and thus are not suitable as a model animal for elucidating the pathogenesis of atopic dermatitis. Further, it has been revealed that a flaky tail (ft) mouse known as a ichthyosis vulgaris mouse model carries a recessive mutation in the vicinity of the gene region encoding loricrin and filaggrin that are proteins constituting the stratum corneum (Non-patent Document 8), and that, in the mouse epidermis, no normal profilaggrin protein (about 500 kDa) is produced, and a mutated profilaggrin protein of a smaller molecular weight (220 kDa) is expressed instead (Non-patent Document 8 and Non-patent Document 9). However, ft mice are considered to be inadequate for a model for atopic dermatitis patients who completely lacks profilaggrin protein and filaggrin protein, since (1) ft mice are spontaneously-generated mutant mice and therefore may carry a mutation in genes other than filaggrin gene, and (2) that even abnormal profilaggrin protein expressed in ft mice may be processed to generate filaggrin protein and filaggrin peptides. As stated above, no animal model has been established so far that has completely lost profilaggrin protein and filaggrin protein, which can be used as an atopic dermatitis model.

PRIOR ART DOCUMENTS

Patent Documents

Patent Document 1: Japanese Laid-Open Patent Application No. 2004-166696
Patent Document 2: Japanese Laid-Open Patent Application No. 2001-321016

Non-Patent Documents

Non-patent Document 1: Matsuoka et al., Int Immuno., 11: 987-994, 1999
Non-patent Document 2: Yoshimoto et al., Nat Immunol., 1: 132-137, 2000
Non-patent Document 3: Yamanaka et al., J Immunol., 165: 997-1003, 2000
Non-patent Document 4: Tsukuba et al., J Biochem (Tokyo)., 134: 893-902, 2003
Non-patent Document 5: Smith et al., Nat genet., 38: 337-342, 2006

Non-patent Document 6: Palmer et al., Nat genet., 38: 441-446, 2006

Non-patent Document 7: Nomura et al., J Allergy Clin Immunol., 119: 434-440, 2007

Non-patent Document 8: Rothnagel et al., Genomics, 23: 450-456, 1994

Non-patent Document 9: Presland et al., J Inv Dermatol., 115: 1072-1081, 2000

Non-patent Document 10: Kitagaki H, et al. J Invest Dermatol 105: 749-755, 1995

Non-patent Document 11: Spergel J M, et al. J Clin Invest 101: 1614-1622, 1998

Non-patent Document 12: Fallon PG. et al., Nat genet 41: 602-608, 2009

DISCLOSURE OF THE INVENTION

Object to be Solved by the Invention

The object of the present invention is to provide a mouse model for allergic diseases such as atopic dermatitis or a dermatitis mouse model with impaired skin-barrier function.

Means to Solve the Object

The present inventors first decided to examine the expression of profilaggrin protein and filaggrin protein in flaky tail (ft) mice for studying if ft mice that are an ichthyosis vulgaris mouse model can also be used as a model for atopic dermatitis patients as stated above. Skin extract from an ft mouse having a nonsense mutation on the sixth filaggrin repeat in the filaggrin gene (Non-patent Document 12) was electrophoresed and then Western blotting was performed by using an antibody against the repetitive region of profilaggrin protein (Rabbit Anti-Filaggrin Polyclonal Antibody, Unconjugated; Covance Research Products Inc.: Cat# PRB-417P). Consequently, as shown in the rightmost "ft" lanes of FIG. 5-*a*, a band of mutant profilaggrin protein the length of which is about half the length of the band of normal profilaggrin protein, as well as several bands in the course of processing into filaggrin protein, and further a weak band of mature filaggrin protein were observed. It is considered that filaggrin protein, after it has been finally degraded into amino-acid level, functions as a natural moisturizing factor and thus contributes to moisturizing the skin as well as to the skin-barrier function. Specifically, it was confirmed that, although inadequately as compared with wild-type mice, ft mice express filaggrin protein that can function as a natural moisturizing factor. These results demonstrated that ft mice are inadequate for analyzing the function of filaggrin protein or for analyzing skin-barrier disorder due to lack of filaggrin and pathogenic mechanism of atopic dermatitis triggered by the skin-barrier disorder, and that it is necessary to produce knockout mice that have completely lost the expressions of profilaggrin protein and filaggrin protein.

Subsequently, the present inventors tried to produce a knockout mouse which has completely lost the expressions of profilaggrin protein and filaggrin protein. The mouse filaggrin gene consists of short exon 1 which is an untranslated region, exon 2 containing the translation-initiation site, and very large exon 3 over 10000 bp which is specific to filaggrin. Exon 3 contains a very long translated region and a stop codon. The translated region contained in exon 3 has a special structure, flanked by 5'-end and 3'-end short specific sequences, and comprising 12 continuous repetitive sequences that are highly homologous. Therefore, it was considered that these sequences were susceptible to an unpredictable variation due to a homologous recombination at the time of targeting. In order to prevent such unpredictable variation and non-specific recombination between the repetitive sequences, the present inventors prepared a targeting vector (TV1) by setting a short arm on the side of exon 3 and a long arm on the side of exon 1, respectively, and used the targeting vector to successfully produce a filaggrin gene-deficient mouse that has completely lost the expressions of profilaggrin protein and filaggrin protein.

The present inventors further investigated the phenotype of the filaggrin gene-deficient mouse, and demonstrated that the filaggrin-gene deficient mouse (1) has impaired skin-barrier function as compared with a wild-type mouse; (2) has an high skin permeability and thus a substance come into contact with outside of the skin can easily be taken into Langerhans cells of the skin as an antigen; and (3) is induced to develop dermatitis by a mite antigen. The present inventors thus found that the filaggrin gene-deficient mice are highly useful as a mouse model for dermatitis, and particularly for atopic dermatitis, thereby completed the present invention.

More specifically, the present invention relates to: (1) a method for using a mouse as an allergic disease animal model, wherein an endogenous gene of the mouse encoding filaggrin is entirely or partially disrupted by a genetic mutation such as deletion or replacement, to cause the mouse to lose a function of expressing profilaggrin and filaggrin; (2) the method according to (1), wherein the allergic disease is atopic dermatitis; (3) a method for using a mouse as a dermatitis animal model with impaired skin-barrier function, wherein an endogenous gene of the mouse encoding filaggrin is entirely or partially disrupted by a genetic mutation such as deletion or replacement, to cause the mouse to lose a function of expressing profilaggrin and filaggrin; (4) the method according to any one of (1) to (3), wherein a part of the endogenous gene encoding filaggrin is a region from a translation-initiation site contained in exon 2 through an in-frame ATG contained in exon 3; (5) the method according to any one of (1) to (4), wherein the part of the endogenous gene encoding filaggrin is replaced by a marker gene due to a homologous recombination with a targeting vector having the following characteristics (a) to (c): (a) being designed so that the region from the translation-initiation site contained in exon 2 through the in-frame ATG contained in exon 3of the endogenous gene encoding filaggrin is replaced by the marker gene at the time of homologous recombination; (b) comprising on a 5' side of the marker gene sequence of the above (a), a gene sequence of 7 kb or more which is homologous to a sequence comprising a 5'-untranslated region of the endogenous gene encoding filaggrin; and (c) comprising on a 3' side of the marker gene sequence of the above (a), a gene sequence of 1.5 kb or less which is homologous to a sequence downstream of the in-frame ATG contained in exon 3of the endogenous gene encoding filaggrin; and (6) the method according to any one of (1) to (5), wherein the mouse caused to lose the function of expressing profilaggrin and filaggrin is characterized by the following (a) to (c): (a) a reduced amount of amino acids in stratum corneum as compared with a wild-type mouse of the same strain; (b) a higher skin-permeability as compared with a wild-type mouse of the same strain; and (c) dermatitis that is induced by a mite-allergen sensitization.

The present invention further relates to: (7) an allergic-disease mouse model, wherein a region from a translation-initiation site contained in exon 2 through an in-frame ATG contained in exon 3of an endogenous gene encoding filaggrin of the mouse is replaced by a marker gene to cause the mouse to lose a function of expressing profilaggrin and filaggrin; (8) the mouse according to (7), wherein the allergic disease is atopic dermatitis; (9) a dermatitis mouse model with impaired skin-barrier function, wherein a region from a translation-initiation site contained in exon 2 through an in-frame ATG contained in exon 3 of an endogenous gene encoding filaggrin of the mouse is replaced by a marker gene to cause the mouse to lose a function of expressing profilaggrin and filaggrin; (10) the mouse according to any one of (7) to (9), wherein the region from the translation-initiation site contained in exon 2 through the in-frame ATG contained in exon 3 is replaced by a marker gene due to a homologous recombination with a targeting vector having the following characteristics (a) to (c): (a) being designed so that the region from the translation-initiation site contained in exon 2 through the in-frame ATG contained in exon 3 of the endogenous gene encoding filaggrin is replaced by the marker gene at the time of homologous recombination; (b) comprising on a 5' side of the marker gene sequence of the above (a), a gene sequence of 7 kb or more which is homologous to a sequence comprising a 5'-untranslated region of the endogenous gene encoding filaggrin; and (c) comprising on a 3' side of the marker gene sequence of the above (a), a gene sequence of 1.5 kb or less which is homologous to a sequence downstream of the in-frame ATG contained in exon 3 of the endogenous gene encoding filaggrin; and (11) the mouse according to any one of (7) to (10), which is characterized by the following (a) to (c): (a) a reduced amount of amino acids in stratum corneum as compared with a wild-type mouse of the same strain; (b) a higher skin-permeability as compared with a wild-type mouse of the same strain; and (c) dermatitis that is induced by a mite-allergen sensitization.

The present invention further relates to (12) a targeting vector having the following characteristics (a) to (c): (a) being designed so that a region from a translation-initiation site contained in exon 2 through an in-frame ATG contained in exon 3 of an endogenous gene encoding filaggrin is replaced by a marker gene at the time of homologous recombination; (b) comprising on a 5' side of the marker gene sequence of the above (a), a gene sequence of 7 kb or more which is homologous to a sequence comprising a 5'-untranslated region of the endogenous gene encoding filaggrin; and (c) comprising on a 3' side of the marker gene sequence of the above (a), a gene sequence of 1.5 kb or less which is homologous to a sequence downstream of the in-frame ATG contained in exon 3 of the endogenous gene encoding filaggrin.

Effect of the Invention

As stated above, filaggrin protein is not only involved in the construction of keratin filament in epidermis but also functions as a moisturizing factor after it has been degraded into the peptide level and plays an important part in the skin-barrier function. Use of mice that have completely lost the function of expressing profilaggrin and filaggrin of the present invention as an allergic-disease model animal or dermatitis model animal enables one to analyze the role of filaggrin in the formation and maintenance of skin-barrier function at a molecular level, and to ascertain the involvement of skin-barrier function in allergic diseases and dermatitis, which allows the clarification of pathogenesis of allergic diseases and dermatitis caused by impaired skin-barrier function as well as screening of a substance effective for preventing and treating above conditions. Further, a mouse with impaired skin-barrier function of the present invention can be preferably used as an animal model for clarifying the relation between atopic dermatitis and the development of asthma. Heretofore, a number of animal models have been known to satisfy the clinical definition of atopic dermatitis. However, no model has been reported that correctly reflects the pathogenesis of the disease, from an exposure to an antigen to the establishment of sensitization. Among existing mouse models, repetitive antigen-application models (Non-patent Documents 10 and 11) appear to show the developmental process similar to atopic dermatitis. Sensitization, however, is established in these mice by artificially destroying skin barrier by a mechanical stimulation such as tape stripping or by an occlusive application of antigen using a patch and then applying the antigen to the mice. Specifically, these are models for analyzing what reaction is elicited against an antigen that has passed the barrier and entered the body. In contrast, the mouse model developed atopic dermatitis having lost the function of expressing profilaggrin and filaggrin of the present invention provides the first model for enabling the analysis of what is caused by skin-barrier disorder, particularly in the earliest stage of atopic dermatitis development, from the passage of the skin barrier by an antigen to the establishment of sensitization.

BRIEF DESCRIPTION OF DRAWINGS

FIG. 1 This figure shows a pattern diagram of the design of the mouse filaggrin gene-targeting vector (TV1) of the present invention.

FIG. 2 This figure shows a pattern diagram of a wild-type filaggrin gene (wild-type allele), the targeting vector, and a mutant filaggrin gene (targeted allele) after a homologous recombination. The original start codon and all in-frame ATGs existing in filaggrin gene can be eliminated by replacing the region from the middle of the sequence of exon 2 through a part of exon 3 of the filaggrin gene by a PGK-neo using the targeting vector of the present invention.

FIG. 3 This figure shows the results of Southern blot analysis to genotype the long-arm side of a positive cell (ES clone 832) prepared using the targeting vector of the present invention.

FIG. 4-a This figure shows the results of Southern blot analysis to genotype the long-arm side of an F1 mouse prepared by crossing the chimeric mouse of the present invention with a wild-type mouse.

FIG. 4-b This figure shows the results of Southern blotting to analyze the genotype of the short-arm side of a clone obtained using the BA1 hybrid ES of the present invention.

FIG. 4-c This figure shows the genotypes of a chimeric mouse and an F1 mouse obtained when the 129 mouse-derived genome has been involved in the homologous recombination in a clone obtained using the BA1 hybrid ES of the present invention.

FIG. 4-d This figure shows the genotypes of a chimeric mouse and an F1 mouse obtained when the B6 mouse-derived genome has been involved in the homologous recombination in a clone obtained using the BA1 hybrid ES of the present invention.

FIG. 5-a This figure shows results of Western blotting to detect profilaggrin protein and filaggrin protein existing in the skin extracts from flaky tail mice and the mice of the present invention. In this figure, +/+ represents a wild-type mouse, +/− a heterozygous mouse ($FLG^{+/-}$), −/− a homozygous mouse ($FLG^{-/-}$), and ft a flaky tail mouse, respectively.

FIG. 5-b This figure shows the results of Western blotting to detect profilaggrin protein and filaggrin protein existing in the skin extracts from the $FLG^{+/-}$ mouse and $FLG^{-/-}$ mouse of the present invention. In this figure, +/+ represents a wild-type mouse, +/− a heterozygous mouse ($FLG^{+/-}$), and −/− a homozygous mouse ($FLG^{-/-}$), respectively.

FIG. 6 This figure shows the results of an immunohistochemical-staining to detect profilaggrin protein and filaggrin protein expressions in the dermal tissue from the FLG$^{+/-}$ mouse and FLG$^{-/-}$ mouse of the present invention. In this figure, +/+ represents a wild-type mouse, +/– a heterozygous mouse, and –/– a homozygous mouse, respectively. The photographs, from the top, show staining results using hematoxylin/eosin (HE), filaggrin (FLG), loricrin (LOR), and involucrin (INV).

FIG. 7 This figure shows the results of a comparison between the FLG$^{-/-}$ mouse of the present invention and a wild-type mouse in terms of the amount of amino acid contained in the stratum corneum. In this figure, "wt" represents a wild-type mouse and "KO" a homozygous mouse (FLG$^{-/-}$), respectively.

FIG. 8 This figure shows the results of a comparison between the FLG$^{-/-}$ mouse of the present invention and a wild-type mouse in terms of the types of amino acids contained in the stratum corneum, demonstrating that the FLG$^{-/-}$ mouse showed a marked reduction in amino acids that are abundant in filaggrin. The vertical axis of the figure shows the amount of each amino acid (molar amount) contained in the stratum corneum of the FLG$^{-/-}$ mouse or of the wild-type mouse, while the horizontal axis shows the result of aligning the amino acids from the left to right in the descending order of the amount contained in filaggrin protein. In this figure, "wt" represents a wild-type mouse and "KO" a homozygous mouse (FLG$^{-/-}$), respectively.

FIG. 9 These photographs show observation results of a paw of a wild-type mouse and a FLG$^{-/-}$ mouse with an ordinary scanning electron microscope (without a low-vacuum chamber), after the paws were treated by a conventional critical-point drying method and coated with platinum by vapor deposition.

FIG. 10-a These photographs show observation results of a paw of a wild-type mouse with a low-vacuum scanning electron microscope equipped with a cooling stage at the temperature of –20° C., after the paw was fixed with glutaraldehyde and dried by a t-butylmethanol treatment.

FIG. 10-b These photographs show observation results of a paw of a FLG$^{-/-}$ mouse with a low-vacuum scanning electron microscope equipped with a cooling stage at the temperature of –20° C., after the paw was fixed with glutaraldehyde and dried by a t-butylmethanol treatment.

FIG. 10-c These photographs show observation results of skin collected from the abdomen of a wild-type mouse with a low-vacuum scanning electron microscope equipped with a cooling stage at the temperature of –20° C., after the skin was fixed with glutaraldehyde and dried by a t-butylmethanol treatment. Lower panels show higher magnifications of the squared parts in the upper panels.

FIG. 10-d These photographs show observation results of skin collected from the abdomen of a FLG$^{-/-}$ mouse with a low-vacuum scanning electron microscope equipped with a cooling stage at the temperature of –20° C., after the skin was fixed with glutaraldehyde and dried by a t-butylmethanol treatment. Lower panels show higher magnifications of the squared parts in the upper panels. In these photographs, arrows indicate the parts where immature epidermal layer that is supposed to be covered by corneum under normal conditions is exposed.

FIG. 11-a This figure shows the results of an in vivo molecular concentration analysis of inside of the mouse stratum corneum using an in vivo confocal Raman microscopy (Model 3510; River Diagnostic). In this figure, "wt" represents a wild-type mouse and "KO" a homozygous mouse (FLG$^{-/-}$), respectively.

FIG. 11-b This figure shows the results of an in vivo molecular concentration analysis of inside of the mouse stratum corneum using an in vivo confocal Raman microscopy (Model 3510; River Diagnostic). In this figure, "wt" represents a wild-type mouse and "KO" a homozygous mouse (FLG$^{-/-}$), respectively.

FIG. 12 These photographs show biotin (green) uptake into Langerhans cell bodies (red) in a dermal tissue of the FLG$^{-/-}$ mouse of the present invention. In this figure, +/+ represents a wild-type mouse and –/– a homozygous mouse (FLG$^{-/-}$), respectively.

FIG. 13 These photographs show the results of 8-time alternate-day applications of Dermatophagoides farinae crude antigen to the ear of the FLG$^{-/-}$ mice of the present invention. No sign of dermatitis was observed with a wild-type mouse, while a scab, adherent scales, dilation of blood vessels, and hardening of skin that are the characteristic signs of dermatitis were markedly observed with 2 mice out of 3 of the filaggrin-deficient mice of the present invention.

FIG. 14 These photographs show the results of histological staining after the FLG$^{-/-}$ mice of the present invention went through 16-time alternate-day applications of Dermatophagoides farinae crude antigen to the ear. It was found that auricles of the FLG$^{-/-}$ mice were swollen compared with the wild-type mice and the epidermal tissue was in a spongy state. Further, infiltration of inflammatory cells was observed in the dermis. In this figure, +/+ represents a wild-type mouse and –/– a homozygous mouse (FLG$^{-/-}$), respectively.

BEST MODE OF CARRYING OUT THE INVENTION

The method for using a mouse as a model animal of the present invention is not particularly limited as long as it is a method for using a mouse as an allergic disease model animal or a dermatitis model animal with impaired skin-barrier function, wherein an endogenous gene of the mouse encoding filaggrin is entirely or partially disrupted by a genetic mutation such as deletion or replacement, to cause the mouse to lose the function of expressing profilaggrin and filaggrin, and in particular, a method for using a mouse as an atopic dermatitis and/or asthma model animal can be specifically exemplified. Further, examples of the method for using a mouse as a model animal include use of the mouse in the screening method described hereinbelow and use of the mouse as a model for ascertaining the relation between atopic dermatitis and occurrence of asthma. Further, the allergic-disease mouse model and the dermatitis mouse model, more specifically, the atopic dermatitis mouse model, asthma mouse model, atopic dermatitis/asthma mouse model, etc. of the present invention are not particularly limited as long as they are mice wherein the endogenous gene of the mice encoding filaggrin has been entirely or partially inactivated by a genetic mutation such as disruption, deletion or replacement to cause the mice to lose the function of expressing profilaggrin and filaggrin, resulting in mice with impaired skin-barrier function. Specific examples of the phenotype of the mice include (a) a reduced amount of amino acid in the stratum corneum as compared with wild-type mice of the same strain; (b) a higher skin-permeability as compared with wild-type mice of the same strain; and (c) dermatitis that can be induced by a mite-allergen sensitization.

The skin-barrier function is to retain water in the body or to protect against a substance entering from outside or ultraviolet rays, and the stratum corneum that is the outermost layer of the epidermis fulfils a particularly important function. Filaggrin is produced by the degradation of profilaggrin along with the cornification of keratinocytes, and causes keratin filaments to aggregate. Subsequently, filaggrin is further degraded into low-molecular peptides in the upper layer of stratum corneum, to become a moisturizing factor or ultraviolet absorption factor. Thus, when filaggrin expression is reduced or lost, a normal formation of epidermis, especially the stratum corneum is inhibited and this disturbs water-retaining function and skin-barrier function which protect against an external stimulus. The dermatitis mouse model with impaired skin-barrier function of the present invention can be artificially caused to develop dermatitis by applying a specific stimulus. The above special stimulus is not particularly limited as long as it can cause the development of dermatitis of the mouse model of the present invention, and examples of the stimulus include a contact of skin with a specific substance such as a mite antigen, administration of a specific substance, exposure to ultraviolet rays, external environmental stimulus such as a specific temperature or humidity, etc., among which, a mite-antigen stimulation is preferably exemplified.

The mouse wherein the function of expressing profilaggrin and filaggrin has been reduced or lost of the present invention is not particularly limited as long as it is a FLG mouse wherein the region from the transcription-initiation site contained in exon 2 through an in-frame ATG contained in exon 3 is replaced by a marker gene so that the mouse is caused to lose the function of FLG gene, and it is preferably a mouse wherein the region from the translation-initiation site contained in exon 2 through the in-frame ATG contained in exon 3 is replaced by a marker gene due to a homologous recombination with a targeting vector having the following characteristics (a) to (c): (a) being designed so that the region from the translation-initiation site contained in exon 2 through the in-frame ATG contained in exon 3 of the endogenous gene encoding filaggrin is replaced by the marker gene at the time of homologous recombination; (b) comprising on the 5' side of the marker gene sequence of the above (a), a gene sequence of 7kb or more which is homologous to a sequence comprising a 5'-untranslated region of the endogenous gene encoding filaggrin; and (c) comprising on the 3' side of the marker gene sequence of the above (a), a gene sequence of 1.5 kb or less which is homologous to a sequence downstream of the in-frame ATG contained in exon 3 of the endogenous gene encoding filaggrin. The method for producing the mouse deficient in TLG-gene function is explained hereinbelow.

FLG gene can be obtained by amplifying a mouse gene library by PCR, etc, and screening the obtained gene fragments using a probe derived from mouse FLG gene. The screened FLG gene is subcloned using a plasmid vector, etc., and can be identified by a restriction-enzyme mapping and DNA sequencing. Subsequently, the gene encoding FLG is entirely or partially replaced by a pMC1-neo gene cassette, etc., and then a gene such as diphtheria toxin A fragment (DT-A) gene and Herpes simplex virus thymidine kinase (HSV-tk) gene is introduced into the 3'-end side, to prepare a targeting vector.

The prepared targeting vector is linearized and then introduced into an ES cell by electroporation, etc., for homologous recombination. From among the homologous recombinants, homologously recombined ES cells are selected using antibiotics such as G418 and Ganciclovir (GANC). Further, it is preferred to confirm by Southern blotting, etc., if the selected ES cells are intended recombinants. The confirmed ES-cell clone is microinjected into a mouse blastocyst, and then the blastocyst is returned to a host-parent mouse to produce a chimeric mouse. By crossing this chimeric mouse with a wild-type mouse, a heterozygous mouse (F1 mouse: $FLG^{+/-}$) of the present invention can be obtained, and by crossing the heterozygous mice, a homozygous $FLG^{-/-}$ mouse of the present invention can be obtained. It is also possible to obtain a $FLG^{-/+}$ mouse by crossing the $FLG^{-/-}$ mouse with a wild-type mouse. Examples of the method of confirming a filaggrin expression in the $FLG^{-/+}$ and $FLG^{-/-}$ mice include a method of confirming the gene expression in the above mouse cell or tissue by Northern blotting, RT-PCR, etc., and a method of confirming the protein expression by Western blotting, immunostaining, etc., and Western blotting and immunohistochemical staining are preferred for confirming filaggrin protein and profilaggrin protein expressions in dermal tissue of the mouse. Among the above method, Western blotting with the use of an antibody (Rabbit Anti-Filaggrin Polyclonal Antibody, Unconjugated; Covance Research Products Inc.; Cat# PRB-417P) against the repetitive region of profilaggrin protein is particularly preferred for the confirmation, since this enables the detection of proteins over the gradual degradation process from profilaggrin to filaggrin.

The impaired skin-barrier function of the created $FLG^{-/-}$ mouse can be confirmed noninvasively, for example, by a visual observation of the appearance, measurements of corneum water content and corneum amino-acid content, etc. In addition, further confirmation is possible by a histological examination of a hematoxylin/eosin-stained epidermal-tissue segment of the $FLG^{-/-}$ mouse under a microscope or by observing a t-butylmethanol-treated dermal tissue of the mouse under a low-vacuum scanning electron microscope. Further, the corneum-barrier permeability of the created $FLG^{-/-}$ mouse can be confirmed by a method of evaluating keratin-barrier transmission using sulfo-NHS-LC-biotin which is a cell membrane-impermeable protein-biotinylating reagent, as described in Examples hereinbelow.

One embodiment of the method for using a mouse as a model animal of the present invention is a method for screening an allergy-inducing substance or allergy-suppressing substance that affects via an epicutaneous exposure the immune response of an animal with impaired skin-barrier function. The screening method is not particularly limited as long as it is a screening method comprising administering to and/or exposing the $FLG^{-/-}$ mice of the present invention to a test substance, and comparing/evaluating a change in the phenotypes manifested by individual animals, tissues, organs or cells of the mice with that of wild-type mice of the same strain having been administered and/or exposed to the test substance. In the screening, it is preferred to compare the $FLG^{-/-}$ mouse that has lost the function of expressing filaggrin with a wild-type littermate. The method of administering to and exposing the mouse to a test substance can be selected depending on the property of the test substance, and examples include an oral administration, nasal administration, subcutaneous injection, cutaneous application, cutaneous contact, spraying, etc. Further, the change in phenotypes is not particularly limited as long as it is a change in phenotypes manifested by individual animals, tissues, organs or cells, and preferred examples include a change in the degree of an inflammatory skin condition that is similar to atopic dermatitis, a change in the degree of bronchial asthma condition, etc. The change in the degree of an inflammatory skin condition that is similar to atopic dermatitis can be compared and evaluated, for example, by observing skin appearance, counting the number of scratching behaviors, measuring blood IgG and/or IgE levels, detecting immunocyte infiltration in epidermal tissues, and measuring cytokine production in epidermal cells. Further, the change in the degree of bronchial asthma condition can be compared and evaluated, for example, by detecting immunocyte infiltration in pulmonary-bronchus tissues, measuring airway resistance pressure, measuring nasal resistance, and measuring nasal volume. It is also possible to compare/evaluate the degree of the inflammatory skin condition similar to atopic dermatitis and the degree of bronchial asthma condition at the same time.

Another embodiment of the method for using a mouse as a model animal of the present invention is a method for screening a preventive/therapeutic agent for allergic diseases. The screening method is not particularly limited as long as it is a screening method comprising administering to or exposing the FLG$^{-/-}$ mice of the present invention to a test substance and an allergy-inducing substance, and comparing/evaluating a change in the phenotypes manifested by individual animals, tissues, organs or cells with a case where mice have not been administered and/or exposed to the test substance. In the screening, it is preferred to compare/evaluate the FLG$^{-/-}$ mice with wild-type littermate mice. The method of administering to and/or exposing the mice to the test substance and the allergy-inducing substance can be selected depending on the property of the test substance, and examples include an oral administration, nasal administration, subcutaneous injection, cutaneous application, cutaneous contact, spraying, etc. Further, the mice can be administered and/or exposed to a test substance and an allergy-inducing substance at the same time, or administered and/or exposed to either of the test substance or the allergy-inducing substance first. Further, the allergy-inducing substance is not particularly limited and preferred examples include mite antigens. The method of stimulating with an antigen using allergy-inducing substance is not particularly limited, and examples include a method comprising dissolving the allergy-inducing substance in an appropriate solvent, applying the solution to the mouse skin (sensitization), and repeating applications (induction, challenge) two or more times at a certain interval (for example, several days). The sensitization site and the induction site may be the same or different. Further, the change in phenotypes is not particularly limited as long as it is a change in phenotypes manifested by individual animals, tissues, organs or cells, and preferred examples include a change in the degree of an inflammatory skin condition that is similar to atopic dermatitis, a change in the degree of bronchial asthma condition, etc. The change in the degree of an inflammatory skin condition that is similar to atopic dermatitis can be compared and evaluated, for example, by observing skin appearance, counting the number of scratching behaviors, measuring blood IgG and/or IgE levels, detecting immunocyte infiltration in epidermal tissues, and measuring cytokine production in epidermal cells. Further, the degree of bronchial asthma condition can be compared and evaluated, for example, by detecting immunocyte infiltration in pulmonary-bronchus tissues, measuring airway resistance pressure, measuring nasal resistance, and measuring nasal volume. It is also possible to compare/evaluate the degree of the inflammatory skin condition similar to atopic dermatitis and the degree of bronchial asthma condition at the same time.

The targeting vector of the present invention is not particularly limited as long as it is designed to lose filaggrin-gene function by at least a partial deletion or replacement of the sequence, and/or an insertion of other sequence, in the upstream and/or in the expression region of the gene encoding filaggrin. It is preferred that the vector is designed to allow an insertion of a gene sequence that functions as a marker for positively and/or negatively select ES-cell recombinants, and further to prevent a non-specific recombination due to repetitive sequences of filaggrin gene. A specific and a preferred example of the targeting vector is the one designed so that the region from the translation-initiation site contained in exon 2 through an in-frame ATG contained in exon 3 of the endogenous gene encoding filaggrin is replaced by a marker gene, which targeting vector comprises at the 5' side of the marker gene sequence a gene sequence of 7 kb or more which is homologous to a sequence comprising a 5'-untranslated region of the endogenous gene encoding filaggrin; and at the 3' side of the marker gene sequence a gene sequence of 1.5 kb or less which is homologous to a sequence downstream of the in-frame ATG contained in exon 3 of the endogenous gene encoding filaggrin.

The present invention will be described more specifically with reference to the following examples, while the technical scope of the present invention will not be limited to these exemplifications.

EXAMPLE 1

(Targeting-vector design)
A mouse filaggrin (mFLG) gene consists of short exon 1 which is an untranslated region, exon 2 containing the translation-initiation site, and very large exon 3 over 10000 bp which is specific to filaggrin. Exon 3 has a special structure in that immediately after the start of exon 3, there is an in-frame ATG, and the region from the starting point though approximately 700 bp therefrom is a specific sequence, and 16 repetitive sequences of about 750 bp per span are repeated downstream of the specific sequence. For this reason, it is considered that only disrupting ATG of exon 2 and thus the translation being started from the in-frame ATG immediately after the start of exon 3 will result in an almost normal translation of the full-length filaggrin gene. Therefore, when constructing the targeting vector, it was designed to lack about 1.9 kb comprising the whole region from ATG of exon 2 through ATG of exon 3 (FIG. 1). Further, to avoid the repetitive sequences as much as possible, the long arm was set on the upstream side and the short arm was set on the downstream side. In order to delete the exon 3 ATG, it is necessary to set the short arm downstream of the exon 3 ATG. However, if it is too short, the targeting efficiency is very much adversely affected, and therefore it is not possible to make the short arm too short. Thus, the first 500 bp sequence of a repetitive sequence which is about 750 bp per span was added to the specific sequence of about 700 bp after the exon 3 ATG to prepare a short arm with the length of approximately 1200 bp.

EXAMPLE 2

(Construction of Targeting Vector)
BAC clones (RP23-346B13 and RP23-39E22) comprising mFLG gene locus was obtained. Two primers shown by SEQ ID NOs: 1 and 2 were synthesized; and a genomic DNA sequence comprising filaggrin gene (the range flanked by the above primers in genomic DNA of chromosome 3) necessary for constructing the targeting vector was cloned from the BAC clones using sRed/ET system manufactured by Gene Bridges, which was further subcloned into a Backbone vector. Next, to insert a neo cassette, the sequence (GAATTC (SEQ ID NO:4)) recognized by restriction enzyme EcoRI was created on the translation-initiation site of exon 2 by an in vitro mutagenesis (changed from GATGTC (SEQ ID NO:6) to GGATCC (SEQ ID NO:7), and the sequence (CGTACG (SEQ ID NO:5)) recognized by restriction enzyme BsiWI was created on the first region of exon 3 by an in vitro mutagenesis (CAAATG (SEQ ID NO:8) >>CGTACG (SEQ ID NO:5)). Then, after treated with restriction enzymes EcoRI and BsiWI, Frt/loxP-neo sequence (SEQ ID NO: 3)

that had been cleaved with EcoRI-BsiW1 at both ends was inserted to prepare targeting vector TV1.

EXAMPLE 3

(Preparation of ES and Identification of Positive Clones by Southern Blot Analysis)

First, an introduction of TV1 by electroporation was attempted using C56BL6 ES cells, but no positive cells were obtained. Consequently, the cells used were changed to BA1 hybrid (hybrid of a B6 mouse and a 129 mouse) ES cells, to introduce TV1 by electroporation again.

PCR is commonly used to identify positive clones. In this experiment, however, identifying positive cells by PCR was not possible due to the repetitive sequences of the filaggrin gene. Therefore, it was decided to perform Southern blot analysis to search for positive clones using the sequence immediately preceding the repetitive sequences as a probe. The position of the probe is shown in FIG. 2. As stated above, the short arm comprises the first 500 bp sequence of a repetitive sequence of filaggrin gene, and sequences that match almost 100% with the above 500 bp sequence appear 15 times repeatedly downstream of the short arm. Consequently, an unexpected homologous recombination may occur somewhere in the 16 repetitive sequences (about 750 bp per span) on the short-arm side. Thus it is necessary to perform Southern blot analysis of the short-arm side to prove that the homologous recombination at the short-arm side has occurred correctly. In common Southern blot analysis, a sequence outside the short arm (i.e., the sequence not included in the targeting vector) is used to prepare a probe. In this targeting vector, however, there are repetitive sequences outside the short arm, which prevented the probe from being prepared outside the short arm. Consequently, the probe was prepared within the short arm of the targeting vector. Further, a genomic-cleavage restriction enzyme to be used in Southern blotting was searched to find out that only MscI can be used (FIG. 2). As stated above, filaggrin gene comprises 15 repetitive sequences, but they are not repetitions of exactly the same sequences, but respective repetitive sequences comprise a part which is different from sequence to sequence. The sequence recognized by MscI is in such sequences that are different in respective sequences. Therefore, it is possible to detect clones having a homologous recombination occurred at the correct site by performing Southern blot analysis using the above probe after digesting the genomic DNA with MscI. Further, even clones having a recombination occurred at an unexpected site were also considered detectable because this shifts the position of the band to be detected.

The clones obtained using the BA1 hybrid ES was genotyped by the above Southern blot analysis, and consequently, two bands of 10 kb and 6 kb were detected entirely unexpectedly (FIG. 4-a, lane 3 and 11). It was estimated that this resulted from the fact that B6-mouse and 129-mouse hybrid ES cells were used for preparing the ES clones. Thus, the B6-mouse and 129-mouse genomes were cleaved with MscI respectively, and subjected to Southern blot analysis. Consequently, it was revealed that the 10 kb band was derived from the 129-mouse genome, and the 6 kb band was from the B6-mouse genome. Further, from the size of the bands, it was considered that there is polymorphism for the sites recognized by MscI within the repetitive sequences of filaggrin gene. Such gene polymorphism inside an exon is very rare, and was considered to be specific for genes having repetitive sequences that are susceptible to mutations. This polymorphism made the analysis thereafter even more difficult. First, Southern blot analysis was performed on the long-arm side of the clones obtained by the targeting, to obtain clone #824 having the homologous recombination of interest on the long-arm side (FIG. 3). Next, the #824 genome was cleaved with MscI and subjected to Southern blotting, which indicated 10 kb and 6 kb bands. Therefore, it was considered that this clone is very likely to have the homologous recombination at the correct site on the short-arm side, too. However, at this stage, it was not clear which filaggrin gene, either from B6 genome or 129 genome, was involved in the homologous recombination in clone #824.

(Production of Chimeric Mouse)

By transplanting a blastocyst introduced with the ES clone #824 to a host parent, a chimeric mouse was produced which was further mated with a B6 mouse to provide a F1 heterozygous mouse (additional FIGS. 4-b and c). The genome of this F1 heterozygous mouse was cleaved with MscI and subjected to Southern blot analysis. Only a 6 kb band was obtained from the F1 heterozygous mouse. This result finally verified at this stage, that a homologous recombination had occurred correctly in the filaggrin gene of the B6 mouse-derived genome and not in the filaggrin gene of the 129 mouse-derived genome. This method of confirming whether a homologous recombination has occurred at the right position in the targeting of the present invention is a highly unique method that have been developed by addressing the extreme specificity of repetitive sequences in filaggrin gene.

EXAMPLE 4

(Analysis of Filaggrin-Expression in FLG-Gene Deficient Mouse)

Western blot analysis and immunohistochemical staining were performed to confirm a specific reduction or loss of filaggrin-protein expression in the $FLG^{+/-}$ mouse and $FLG^{-/-}$ mouse produced in Example 3.

FIG. 5-a shows the results of Western blotting which detected profilaggrin protein and filaggrin protein in the skin extracts from flaky tail mice and the mice of the present invention. For wild-type mice (+/+), heterozygous mice (+/−), and filaggrin knockout mice (−/−), a band of profilaggrin protein which is filaggrin precursor, a ladder-like band showing profilaggrin protein gradually degraded, and a band of mature filaggrin protein were observed. In contrast, these bands have been completely lost for the knockout mice. Based on the above, the followings have been demonstrated: (1) that the antibody used was a filaggrin-specific antigen and recognizes no other protein than filaggrin; and (2) that neither profilaggrin protein nor filaggrin protein has been produced in the filaggrin-knockout mice. Further, for the flaky-tail mice, a band of mutant profilaggrin protein which was about half the length of the band of normal profilaggrin protein and a weak band of mature filaggrin protein were observed.

FIG. 5-b shows the results of Western blotting to examine the expressions of corneum-localized proteins in skin extracts from wild-type mice (+/+), heterozygous deficient mice (+/−), and homozygous deficient mice (−/−). As stated above, neither profilaggrin protein nor filaggrin protein was detected for $FLG^{-/-}$ mice, while loricrin and involucrin that are representative keratin-localized proteins were expressed in all of the wild-type, $FLG^{+/-}$, and $FLG^{-/-}$, and no significant difference in the expression level was observed. It was confirmed by the constant expression level of the control β-actin that the same amount of sample was allowed to migrate in each lane.

FIG. 6 shows the results of an immunohistochemical staining to examine filaggrin protein expression in the dermal tissue of a wild-type mouse (+/+), heterozygous deficient mouse (+/−), and homozygous deficient mouse (−/−). Consistent with the experimental results of the above Western blotting, no filaggrin protein was detected for the FLG$^{-/-}$ mouse, while loricrin (LOR) and involucrin (INV) were expressed at the similar level in all of the wild-type, FLG$^{-/+}$ and FLG$^{-/-}$. No distinct difference was seen among the above mice, from the results of hematoxylin/eosin (HE) staining.

The above results ascertained that the dermal tissues of the FLG$^{-/-}$ mouse completely lost the expression of filaggrin protein.

EXAMPLE 5

(Phenotype Analysis of FLG-Gene-Deficient Mouse)

The following comparative experiment was performed using a FLG$^{-/-}$ mouse, FLG$^{+/-}$ mouse, and wild-type littermate mouse.

(Analysis of Corneum Amino-Acid Composition)

The level and types of amino acid contained in stratum corneum were analyzed using a FLG$^{-/-}$ mouse and a wild-type mouse at 4 days of age. Stratum corneum samples were collected from a 1.5×2.0 cm$^2$ region of mouse dorsal skin by repeating tape-stripping 6 times in total using mending tape (Scotch). Stratum corneum was extracted from the mending tape using toluene by 4 separate operations in total. The extract was evaporated to remove the solvent, dissolved in a 10% sulfosalicylic acid, and subjected to an amino-acid analysis with an amino-acid analyzer (Hitachi). Consequently, the molar amount of amino acid per unit area of stratum corneum in the FLG$^{-/-}$ mouse was markedly reduced compared with the wild-type mouse (FIG. 7). In FIG. 8, the vertical axis shows the level of each amino acid (molar amount) contained in the stratum corneum of the FLG$^{-/-}$ mouse or the wild-type mouse, and the horizontal axis shows the results of aligning the amino acids from the left to right in the descending order of the amount contained in filaggrin protein. This figure demonstrates that more abundantly an amino acid is contained in filaggrin protein, more markedly the amount of amino acid is reduced, while the figure also shows that the amount of amino acids that are not contained in filaggrin protein as much as the above abundant amino acids has also been reduced. Above results ascertained that the amino-acid level within stratum corneum is reduced in FLG$^{-/-}$ mice.

(Corneum Tissue Analysis with Low-Vacuum Scanning Electron Microscope)

Skin was collected from a FLG$^{-/-}$ mouse and a wild-type mouse at 5 days of age and was fixed with glutaraldehyde. After dried by a t-butylmethanol treatment, the skin was observed under a low-vacuum scanning electron microscope equipped with a cooling stage at the temperature of −20° C. (Hitachi S-3400N; Hitachi). As can be seen from the results of FIG. 10-*a* to FIG. 10-*d*, by selecting t-butylethanol, the morphology of skin surface can be well retained, and by selecting the low-vacuum scanning electron microscope, tissue destruction due to vacuum can be minimized, which allows an observation of the original morphology. The low-vacuum scanning electron microscope was used in 2 different modes, to detect either reflection electron or secondary electron.

FIG. 10-*a* and FIG. 10-*b* show observation results of a paw, where the stratum corneum is physiologically thick. It was observed that the skin surface of the wild-type mouse paw was covered with layered corneum, like an armor (FIG. 10-*a*), whereas the skin surface of the filaggrin-deficient mouse was smooth, and had thin stratum corneum (FIG. 10-*b*). These results implied that loss of filaggrin may result in an inability to form a normal layered structure of corneum.

FIG. 10-*c* and FIG. 10-*d* show observation results of skin of the body trunk (abdomen). Lower panels show higher magnifications of the squared parts in the upper panels. It was observed that the skin surface of the wild-type mouse was covered by the layered stratum corneum or the stratum corneum with a ribbon-like pattern, whereas the filaggrin-deficient mouse had many parts lacking this structure, and the underlying nucleated-cell layer could be seen through. The above results suggested that in wild-type mice, the stratum corneum forms an outermost skin barrier having a layered structure, whereas this structure is not formed normally or desquamates easily in filaggrin-deficient mice and thus immature skin-surface layer is exposed which is supposed to be covered by corneum under normal conditions.

As a control experiment for the above experiment, FIG. 9 shows results of ordinary scanning-electron microscopic observations (without a low-vacuum chamber) performed after the paw was subjected to a conventional critical-point drying and a platinum coating by vapor deposition. It was extremely difficult to determine the phenotypes because of the strongly-induced tissue artifact due to pretreatment of the samples and the low vacuum of the sample chamber of the scanning electron microscope.

(Analysis of Molecule Concentrations within Stratum Corneum)

Molecule concentrations within mouse stratum corneum were analyzed in vivo using an in vivo confocal raman spectrometer (Model 3510; River Diagnostic). 5 mice each of FLG$^{-/-}$ and wild-type, 2 to 5 days of age were provided, and molecule concentrations in the stratum corneum were measured in the mice, from the abdominal skin surface up to the depth of 8 μm that was within the mouse stratum corneum thickness, with intervals of 2 μm. A 785 nm laser was used as a light source to examine a 400 to 1800 cm$^{-1}$ region called a finger print region, and various amino acids and metabolites thereof were quantified. NMF (Natural Moisturizing Factor) was determined by the sum of raman spectra for the main components, i.e., serine, glycine, pyrrolidone-5-carboxylic acid (PCA), proline, ornithine, histidine (pH4), histidine (pH7), and alanine.

Molecule-concentration profiles of NMF, various amino acids, etc. shown in figures have been calculated as relative values for each of these molecules, using the signal intensity of raman spectrum of keratin as the reference value, since this spectrum was considered to be least different between the FLG$^{-/-}$ mice and wild-type mice. As can be seen from the results of FIG. 11-*a* and -*b*, it has been revealed that component called natural moisturizing factor is markedly reduced in FLG$^{-/-}$ mice. As expected, the above results suggested that water content in the stratum corneum of FLG$^{-/-}$ mice was markedly reduced and thus the skin was drier compared with the wild-type stratum corneum.

(Analysis of Skin-Barrier Function of FLG-Gene-Deficient Mouse)

To confirm that the skin-barrier function is impaired in FLG-gene deficient mice, a method was developed for evaluating skin-barrier function based on the amount of uptake of antigen into Langerhans cells that are antigen-presenting cells in epidermis, to examine the skin-barrier function in FLG$^{-/-}$ mice and wild-type mice.

In a conventional method for evaluating antigen uptake into Langerhans cells by externally applying antigen to the skin, reagents such as FITC that easily pass through the corneum barrier has been used. However, a change in the corneum-barrier transmission due to loss of filaggrin cannot be observed by the methods using reagents that easily pass through the corneum barrier. Thus the present inventors established for the first time a method for evaluating corneum-barrier transmission using sulfo-NHS-LC-biotin which is a cell-membrane impermeable, protein-biotinylating reagent. This method has enabled the observation of a change in corneum-barrier transmission. The structural formula of sulfo-NHS-LC-biotin is shown below.

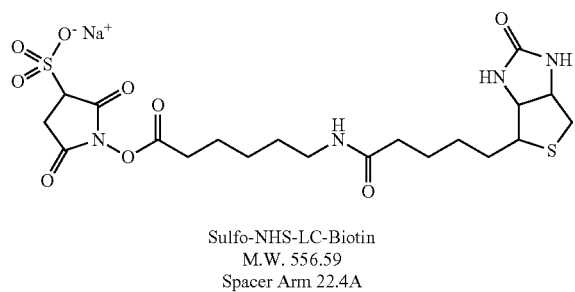 [SMILES: O=C(CCCCC1SCC2NC(=O)NC21)NCCCCCC(=O)ON1C(=O)CC(S(=O)(=O)[O-])C1=O ; [Na+]]

Sulfo-NHS-LC-Biotin
M.W. 556.59
Spacer Arm 22.4A

Sulfo-NHS-LC-biotin (#21335; Thermo Scientific) was applied to a FLG$^{-/-}$ mouse and a wild-type littermate mouse at 7 weeks of age on the skin surface inside the ear, and the uptake into Langerhans cells was observed under a fluorescence microscope. Specifically, sulfo-NHS-LC-biotin [10 mg/mL in PBS/0.7 mM CaCl$_2$] was applied to the skin surface, and the ears were collected from the mice after 24 hours. The skin of the ear was stripped from the cartilage and treated with 3.8% ammonium thiocyanate/phosohoric acid buffer at 37° C. for 20 minutes, and the epidermis was stripped mechanically from the dermis. Then, the epidermis was fixed with 95% ethanol, and Langerhans cells were stained with anti-MHC Class II IA+IE antibody [M5/114.15.2] (eBioscience) and biotinylated protein was stained with avidin-Alexa 488 (Invitrogen), which were then observed under a Leica TCS SP5 laser confocal microscope (Leica).

As shown in FIG. 12, no biotin (green) uptake into Langerhans cells (red) was observed in the wild-type mouse, whereas in the FLG$^{-/-}$ mouse, the microscopic images were frequently obtained where biotin (green) taken up was accumulated in Langerhans cell body (red) (indicated by arrows). These results indicated that skin-barrier function was disturbed in the FLG$^{-/-}$ mouse and that the substance applied to the outside of corneum easily penetrated the skin barrier and entered the epidermis and then taken up as an antigen by Langerhans cells.

EXAMPLE 6

(Induction of Dermatitis by Mite-Antigen Sensitization)

First, it was examined if a sensitization can be easily established in FLG$^{-/-}$ mice to a transdermally applied antigen. Dermatophagoides farinae crude antigen was applied on alternate days to FLG$^{-/-}$ mice (n=3) and wild-type littermate mice (n=4) at 6 to 8 weeks of age on both ears, respectively. FIG. 13 shows the photographs after 8-time applications. As shown in FIG. 13, a crust, adhered scaly skin, vascular dilation, and hardening of skin that are symptoms found in dermatitis, were significant on 2 out of 3 filaggrin-deficient mice, while no apparent symptoms of dermatitis were observed on all 4 wild-type littermate mice. Specifically, it was considered that FLG$^{-/-}$ mice were susceptible to transdermal sensitization to an antigen.

Further, dermatophagoides farinae crude antigen was applied 16 times to FLG$^{-/-}$ mice and wild-type littermate mice, then the ears were collected from the mice and subjected to hematoxylin/eosin (HE) staining to examine histological changes. As shown in FIG. 14, the auricle of the ear of FLG$^{-/-}$ mice was swollen (thickness increased) compared with wild-type mice, and in the epidermis part (the part with darker color in the photographs), the gap between the cells were seen as decolorized spaces, which demonstrated that the epidermal tissue was in a spongy state. Further, infiltration of inflammatory cells was observed in the dermis.

EXAMPLE 7

(Analysis of Mechanism of Increased Antigen-Sensitization in Filaggrin-Deficient Mouse)

There are two prominent possibilities for the mechanism of how increased susceptibility to antigen sensitization is established in skin due to lack of filaggrin: (1) lack of filaggrin weakens the stratum-corneum barrier of the skin and thus it becomes easier for the antigen to pass the skin and to be exposed to the immune system; and (2) the interaction between the skin and cells of the immune system is modulated by lack of filaggrin, which causes the skin to become increasingly susceptible to an antigen sensitization. For the above (1), stratum corneum-barrier transmission and permeability of skin were measured for various substances using a raman spectrometer, two-photon microscope, and mass microscope. Further, antigen passed through the skin and then taken up by antigen-presenting cells was quantitatively analyzed by FACS (flow cytometry), thereby the change in the level of antigen that passed the skin was measured. Meanwhile, as for the above (2), the effect of lack of filaggrin was measured in terms of the degree of various antigen-presenting cell activations in the epidermis and dermis under a steady condition or in a tape stripping or patch test.

EXAMPLE 8

(Development of Barrier-Function Replenishing Drug for Skin-Barrier Disorder Due to Loss of Filaggrin)

A dermatitis model which was a filaggrin-knockout mouse was used for screening an agent than can prevent the initiation of dermatitis by replenishing the barrier function.

EXAMPLE 9

(Development of a Mouse Model for Atopic Dermatitis by Chronically Stimulating with Antigen)

As demonstrated above, filaggrin-knockout mice are susceptible to transdermal antigen sensitization. More specifically, patients with atopic dermatitis carrying a filaggrin mutation are considered to become chronically sensitized to transdermal antigen shortly after birth. By using filaggrin-knockout mice, mouse models are developed for atopic dermatitis caused by chronically stimulating with antigen.

EXAMPLE 10

Analysis of Role of Antigen-Presenting Cells in Atopic Dermatitis Model

It is considered that transdermally entered antigen is captured by epidermal Langerhans cells and dermal dendritic cells and then presented to the immune system. It has been recently reported that there are plural subsets of the dermal dendritic cells. However, respective roles played by the epidermal Langerhans cells and each of the dermal dendritic cell subsets in antigen presentation are largely unknown. The Filaggrin-knockout mouse was mated with a Langerin-DTA mouse, Langerin-DTR mouse, and CD11c-DTR mouse to produce filaggrin-knockout mice lacking various antigen-presenting cells of skin, for elucidating the roles played by each of the various antigen-presenting cells in the initiation of atopic dermatitis. A new method is developed for preventing the initiation of and treating atopic dermatitis by suppressing the functions of these antigen-presenting cells or activating the function of antigen-presenting cells that positively affects immunological tolerance.

The invention claimed is:

1. A transgenic mouse whose genome comprises a homozygous disruption of its filaggrin gene wherein a region from a translation-initiation site contained in exon 2 through an in-frame ATG contained in exon 3 of the filaggrin gene is systematically and homozygously replaced by a marker gene via a homologous recombination with a targeting vector having the following characteristics (a) to (c):
  (a) being designed so that the region from the translation-initiation site contained in exon 2 through the in-frame ATG contained in exon 3 of an endogenous gene encoding filaggrin is replaced by the marker gene at the time of homologous recombination;
  (b) comprising on a 5' side of the marker gene sequence of the above (a), a gene sequence of 7 kb or more which is homologous to a sequence comprising a 5'-untranslated region of the endogenous gene encoding filaggrin; and
  (c) comprising on a 3' side of the marker gene sequence of the above (a), a gene sequence of 1.5 kb or less which is homologous to a sequence downstream of the in-frame ATG contained in exon 3 of the endogenous gene encoding filaggrin, wherein the transgenic mouse exhibits the following phenotypes (i) to (iii):
  (i) a reduced amount of amino acids in stratum corneum as compared with a wild-type mouse of the same strain;
  (ii) a higher skin-permeability as compared with a wild-type mouse of the same strain; and
  (iii) dermatitis that is induced by a mite-allergen sensitization.

* * * * *

SEQUENCE LISTING

```
<160> NUMBER OF SEQ ID NOS: 8

<210> SEQ ID NO 1
<211> LENGTH: 83
<212> TYPE: DNA
<213> ORGANISM: Artificial
<220> FEATURE:
<223> OTHER INFORMATION: primer

<400> SEQUENCE: 1
tagagtaaag accctcatct gtaacccagg actttcatcc tacctactct ttgcactgag    60
ccagcggccg catttaaatg gcg                                            83

<210> SEQ ID NO 2
<211> LENGTH: 80
<212> TYPE: DNA
<213> ORGANISM: Artificial
<220> FEATURE:
<223> OTHER INFORMATION: primer

<400> SEQUENCE: 2
tctaaccaag gacacagctc ctctcgccac caggccgact ctcccagggt cagcgcaaga    60
tcgatgatat cagatctgcc                                                80

<210> SEQ ID NO 3
<211> LENGTH: 1796
<212> TYPE: DNA
<213> ORGANISM: Artificial
<220> FEATURE:
<223> OTHER INFORMATION: Neo

<400> SEQUENCE: 3
gaattcgtac gccggcttaa gtgtacacgc gtactagtct agcgaagttc ctatactttc    60
tagagaatag gaacttcccg cggataactt cgtatagcat acattatacg aagttatgtc   120
agcttctgat ggaattagaa cttggcaaaa caatactgag aatgaagtgt atgtggaaca   180
gatctgatat ccagggagct ctcagacgtc gcttggtcgg tctttattcg aaccccagag   240
tcccgctcag aagaactcgt caagaaggcg atagaaggcg atgcgctgcg aatcgggagc   300
ggcgataccg taaagcacga ggaagcggtc agcccattcg ccgccaagct cttcagcaat   360
atcacgggta gccaacgcta tgtcctgata gcggtccgcc acacccagcc ggccacagtc   420
gatgaatcca gaaaagcggc cattttccac catgatattc ggcaagcagg catcgccatg   480
ggtcacgacg agatcatcgc cgtcgggcat gcgcgccttg agcctggcga acagttcggc   540
tggcgcgagc ccctgatgct cttcgtccag atcatcctga tcgacaagac cggcttccat   600
ccgagtacgt gctcgctcga tgcgatgttt cgcttggtgg tcgaatgggc aggtagccgg   660
atcaagcgta tgcagccgcc gcattgcatc agccatgatg gatactttct cggcaggagc   720
aaggtgagat gacaggagat cctgccccgg cacttcgccc aatagcagcc agtcccttcc   780
cgcttcagtg acaacgtcga gcacagctgc gcaaggaacg cccgtcgtgg ccagccacga   840
tagccgcgct gcctcgtcct gcagttcatt cagggcaccg gacaggtcgg tcttgacaaa   900
aagaaccggg cgcccctgcg ctgacagccg gaacacggcg gcatcagagc agccgattgt   960
```

-continued

| | |
|---|---|
| ctgttgtgcc cagtcatagc cgaatagcct ctccacccaa gcggccggag aacctgcgtg | 1020 |
| caatccatct tgttcaatgg ccgatcccat ggtttagttc ctcaccttgt cgtattatac | 1080 |
| tatgccgata tactatgccg atgattaatt gtcaacacgt gctgctgcag gtcgaaaggc | 1140 |
| ccggagatga ggaagaggag aacagcgcgg cagacgtgcg cttttgaagc gtgcagaatg | 1200 |
| ccgggctccg gaggaccttc gcgcccgccc cgcccctgag cccgcccctg agcccgcccc | 1260 |
| cggacccacc ccttcccagc ctctgagccc agaaagcgaa ggagcaaagc tgctattggc | 1320 |
| cgctgcccca aaggcctacc cgcttccatt gctcagcggt gctgtccatc tgcacgagac | 1380 |
| tagtgagacg tgctacttcc atttgtcacg tcctgcacga cgcgagctgc ggggcggggg | 1440 |
| ggaacttcct gactagggga ggagtagaag gtggcgcgaa ggggccacca agaacggag | 1500 |
| ccggttggcg ctaccggtgg atgtggaatg tgtgcgaggc cagaggccac ttgtgtagcg | 1560 |
| ccaagtgcca gcggggctgc taaagcgcat gctccagact gccttgggaa aagcgcctcc | 1620 |
| cctacccggt agagcgcctc ccctacccgg tagaatgaag ttcctatact ttctagagaa | 1680 |
| taggaacttc gttcgaacat aacttcgtat agcatacatt atacgaagtt atggtacctg | 1740 |
| cagaattcat gcataagctt ggatccgttc ttcggacgcc tcgtcaacac cgtacg | 1796 |

<210> SEQ ID NO 4
<211> LENGTH: 6
<212> TYPE: DNA
<213> ORGANISM: Artificial
<220> FEATURE:
<223> OTHER INFORMATION: EcoRI recognizing site

<400> SEQUENCE: 4 gaattc                                                                  6

<210> SEQ ID NO 5
<211> LENGTH: 6
<212> TYPE: DNA
<213> ORGANISM: Artificial
<220> FEATURE:
<223> OTHER INFORMATION: BsiWI recognizing site

<400> SEQUENCE: 5 cgtacg                                                                  6

<210> SEQ ID NO 6
<211> LENGTH: 6
<212> TYPE: DNA
<213> ORGANISM: Artificial
<220> FEATURE:
<223> OTHER INFORMATION: translation-initiation site

<400> SEQUENCE: 6 gatgtc                                                                  6

<210> SEQ ID NO 7
<211> LENGTH: 6
<212> TYPE: DNA
<213> ORGANISM: Artificial
<220> FEATURE:
<223> OTHER INFORMATION: mutated translation-initiation site

<400> SEQUENCE: 7 ggatcc                                                                  6

<210> SEQ ID NO 8
<211> LENGTH: 6
<212> TYPE: DNA

-continued

```
<213> ORGANISM: Artificial
<220> FEATURE:
<223> OTHER INFORMATION: first region of exon 3

<400> SEQUENCE: 8 caaatg                                                                        6
```